United States Patent [19]

Bowman

[11] Patent Number: 4,803,997

[45] Date of Patent: Feb. 14, 1989

[54] MEDICAL MONITOR
[75] Inventor: Bruce R. Bowman, Eden Prairie, Minn.
[73] Assignee: Edentec Corporation, Eden Prairie, Minn.
[21] Appl. No.: 885,231
[22] Filed: Jul. 14, 1986
[51] Int. Cl.$^4$ ............................................. A61B 5/08
[52] U.S. Cl. .................................. 128/723; 128/671; 128/700; 128/716
[58] Field of Search ........ 128/671, 700, 716, 720–723, 128/725; 340/573

[56] References Cited

U.S. PATENT DOCUMENTS

| | | |
|---|---|---|
| 1,619,005 | 3/1927 | Strong . |
| 2,184,511 | 10/1937 | Bagno et al. . |
| 2,235,894 | 3/1941 | Lee . |
| 2,661,734 | 12/1953 | Holzer et al. . |
| 2,831,181 | 4/1958 | Warner . |
| 3,232,288 | 2/1966 | Krobath . |
| 3,302,106 | 1/1967 | Shaw . |
| 3,316,896 | 5/1967 | Thomasset . |
| 3,316,902 | 5/1967 | Winchel et al. . |
| 3,324,848 | 6/1967 | Domeier et al. . |
| 3,340,867 | 9/1967 | Kubicek et al. . |
| 3,347,223 | 10/1967 | Pacela . |
| 3,356,062 | 10/1970 | Horn . |
| 3,433,217 | 3/1969 | Rieke . |
| 3,452,743 | 7/1969 | Rieke . |
| 3,483,861 | 12/1969 | Tiep . |
| 3,513,832 | 5/1970 | Klemm et al. . |
| 3,524,058 | 8/1970 | Robertson et al. . |
| 3,532,087 | 10/1970 | Horn et al. . |
| 3,545,429 | 12/1970 | Pelta . |
| 3,547,106 | 12/1970 | Bornmann . |
| 3,572,316 | 3/1971 | Vogelman et al. . |
| 3,572,317 | 3/1971 | Wade . |
| 3,584,618 | 6/1971 | Reinhard et al. . |
| 3,587,562 | 6/1971 | Williams . |
| 3,608,542 | 9/1971 | Pacela et al. ........................ 128/723 |
| 3,608,543 | 9/1971 | Longini et al. . |
| 3,618,592 | 11/1971 | Stewart . |
| 3,677,261 | 7/1972 | Day . |
| 3,727,606 | 4/1973 | Sielaff . |
| 3,742,936 | 7/1973 | Blanie et al. . |
| 3,802,417 | 4/1972 | Lang . |
| 3,802,419 | 4/1974 | Yates . |
| 3,871,359 | 3/1975 | Pacela . |
| 3,871,360 | 3/1975 | Van Horn et al. . |
| 3,875,481 | 4/1975 | Miller et al. . |
| 3,875,929 | 4/1975 | Grant . |
| 3,882,851 | 5/1975 | Sigworth . |
| 3,888,240 | 6/1975 | Reinhold, Jr. et al. . |
| 3,915,154 | 10/1975 | Cosentino . |
| 3,926,177 | 12/1975 | Hardway Jr. et al. . |
| 3,976,052 | 8/1976 | Junginger et al. . |
| 3,996,922 | 12/1976 | Basham . |
| 4,011,859 | 3/1977 | Frankenburger . |
| 4,031,884 | 6/1977 | Henzel . |
| 4,036,217 | 7/1977 | Ito et al. . |
| 4,116,231 | 9/1978 | Matsuo . |
| 4,129,125 | 12/1978 | Lester et al. . |
| 4,248,240 | 2/1981 | van Eykern . |
| 4,269,195 | 5/1981 | Itoh . |
| 4,270,547 | 6/1981 | Steffen et al. . |
| 4,279,257 | 7/1981 | Hochstein . |
| 4,289,142 | 9/1981 | Kearns . |
| 4,305,400 | 12/1981 | Logan . |
| 4,306,567 | 12/1981 | Krasner . |
| 4,320,766 | 3/1982 | Alihanka et al. . |
| 4,350,166 | 9/1982 | Mobarry . |
| 4,365,636 | 12/1982 | Barker . |
| 4,379,460 | 4/1983 | Judell ................................. 128/671 |
| 4,398,534 | 8/1983 | Hagiwara ....................... 128/303.14 |
| 4,403,215 | 9/1983 | Hofmann et al. . |
| 4,422,458 | 12/1983 | Kravath . |
| 4,449,537 | 5/1987 | Pross et al. .......................... 128/723 |
| 4,506,678 | 3/1985 | Russell et al. ....................... 128/723 |
| 4,580,575 | 4/1986 | Birnbaum et al. .............. 128/723 X |

FOREIGN PATENT DOCUMENTS 2060892 5/1981 United Kingdom ................ 128/716

OTHER PUBLICATIONS

Sahakian et al., "A Multi-Microcomputer . . . Apnec Monitor", Conf.: Proc. 10th Ann NW Bioeng. Conf., Hanover, N.H., Mar. 1982, 151–156.

Primary Examiner—Lee S. Cohen
Attorney, Agent, or Firm—Douglas L. Tschida; Robert J. Klepinski

[57] ABSTRACT

An apnea monitor employs dual detectors for determining patient breaths while rejecting cardiac artifacts. The first detector examines a respiration signal at a first sensitivity for apparent breaths. The second detector examines at a second sensitivity to determine if the apparent breath was actually an artifact.

14 Claims, 20 Drawing Sheets

|  |  |
|---|---|
| FIGURE 3a | FIGURE 3b |
| FIGURE 3c | FIGURE 3d |

FIGURE 3

MEDICAL MONITOR

BACKGROUND OF THE INVENTION

1. Field of the Invention

The present invention relates to medical devices for monitoring patient respiration.

2. Description of the Prior Art

There has long been a need for a medical monitoring device to reliably determine when breathing of a patient ceases. The medical term for this phenomenon is apnea. Since a patient at risk cannot be personally observed at all times, a device is needed to alert medical personnel at times when breathing stops or slows excessively.

It is known that impedance across electrodes mounted on the skin varies with chest motion. The motion of breathing can therefore be detected by sensing such impedance changes. Previous monitors detect each such change as a breath. When the changes do not occur, the devices alert the medical personnel of cessation of breathing.

Prior art monitors have a time period set for the acceptable period during which no breaths are sensed. If the time period is exceeded, an alarm is sounded.

One problem in this sensing is that the range of change in impedance due to breathing overlaps the range of change of impedance due to the mechanical contraction and surge of blood flow resulting from heart beats. Therefore, a heart beat may be mistakenly interpreted as a breath. This unwanted signal is known as a cardiac artifact.

It is desirable to reject these artifacts so they are not erroneously interpreted as breaths. If an artifact is counted as a breath, the apnea timer is restarted. Therefore an apnea alarm may be delayed or not sound at all.

Prior art cardiac artifact rejection, sometimes called coincidence, is based upon cardiac artifact occurring at the same rate as ECG during an apnea. The cardiac artifact is actually not coincident with the electrical ECG signal because it is caused by the physical contraction of the heart and the surge of blood flowing through the body with each contraction which is delayed from the electrical ECG event. There is, however, a one for one correspondence between an ECG and the cardiac artifact which follows.

These prior monitors assume that breathing rarely occurs at the same rate as the heart rate or, it if does, is not sustained for a long period of time. If a prior art monitor begins triggering on cardiac artifact during an apnea, the apparent breath rate will be equal to the heart rate. Based upon this assumption, the prior art devices override the breath detects and invalidate the breath detects until the rates of apparent breaths and heart became unequal. This results in an apnea alarm at the end of the set period.

Prior art monitors depend on the fact that the amplitude of cardiac artifact is either smaller than the monitor's detector sensitivity or large enough that the monitor's detector can consistently detect the artifact. If the amplitude of the cardiac artifact signal is close to the threshold of the breath detector, the breath detector may not consistently detect the cardiac artifact and the apparent breath rate will not be equal to the heart rate. In this case the device cannot make the differentiation between the cardiac artifact and actual breaths. The device may treat some of the ECG artifact as breaths. This results in either a delay or a lack of alert, and a possibly dangerous delay in medical attention.

Examples of the operation of prior art devices appear in FIGS. 1a-c At the top of FIG. 1a is shown the ECG printout, including QRS complexes $Q_0-Q_8$, and ECG detection triggers $ED_0-ED_8$, which are issued for each QRS wave complex in the ECG. Using detection triggers $ED_0-ED_8$ prior art monitors have measured average ECG rate and intervals $ECG_0-ECG_8$ between triggers.

In Case A of FIG. 1a a normal breathing pattern is shown. Also shown are breath detect triggers $BD_{a1}-BD_{a3}$ for the three detected breaths. Between each breath detect trigger $BD_{a1}-BD_{a3}$ is shown a respiratory interval $R_{a1}-R_{a3}$. In this case, respiratory intervals $R_{a1}-R_{a3}$ are not equal to the average heart intervals, shown by intervals $ECG_1-ECG_8$. Additionally, the interval $R_{a1}$ is not equal to the previous ECG interval $ECG_1$. Consequently, breath detect $BD_{a1}$ is accepted as a valid breath by the monitor.

Case B of FIG. 1b illustrates a large cardiac artifact during an apnea. Breath detects $BD_{b1}-BD_{b8}$ are triggered on each artifact. In this case the average breath interval, shown by intervals $R_{b1}-R_{b8}$, is equal to the average ECG interval, shown by intervals $ECG_1-ECG_8$. Also interval $R_{b1}$ is equivalent to interval $ECG_1$, as are intervals $R_{b2}-R_{b8}$ equivalent to intervals $ECG_2-ECG_8$. A prior art monitor with cardiac artifact rejection based on average breath and heart interval equivalency will invalidate breath detects in Case B of FIG. 1b after a certain number of these cardiac artifact detects. Some prior art monitors test for equivalency between the previous respiratory interval and the previous ECG interval. These monitors may disqualify the breath detect following a single cardiac artifact.

Moderate cardiac artifact during an apnea is shown in Case C of FIG. 1c. In this case the amplitude of the cardiac artifact is very close to the threshold of the breath detector of the prior art monitor. For this reason, not every cardiac artifact is detected. The average breath interval, shown by intervals $R_{c1}-R_{c4}$, is not equivalent to the average heart interval, shown by intervals $ECG_1-ECG_8$. Also, interval $R_{c1}$ is not equivalent to interval $ECG_1$. Interval $R_{c2}$ is not equivalent to interval $ECG_3$, but interval $R_{c3}$ is equivalent to interval $ECG_4$. Prior art monitors based on equivalent average intervals will not invalidate any of the three cardiac artifact detects. Prior art monitors based on equivalent previous intervals will not invalidate cardiac artifact detects at breath detects $BD_{c1}$ and $BD_{c2}$, but may invalidate the artifact at detect $BD_{c3}$.

Examples of prior art monitor performance are shown in FIG. 2. FIG. 2 illustrates simulated signals actually used to test prior art monitors and the present invention. FIG. 2 illustrates quiet breathing at 30 breaths per minute, from time t0 to time t1, followed by a large 4 ohm breath sigh. The one-minute apnea ends at time t2, when quiet breathing resumes. The illustration includes a cardiac artifact at 0.25 ohms at the same rate as the ECG, 90 beats per minute.

Graphs of sensing of prior art monitors A-C, and the present invention, have a vertical bar for each event which is detected and validated as a breath by the monitor.

Prior art monitor A uses the breath and ECG rate averaging method of rejecting cardiac artifact. When the average breath rate reaches within a certain percent of the ECG rate, cardiac rejection circuitry invalidates the breath detections until the respiration rate is less than a certain percent of the ECG rate.

Prior art monitor A detects once for each breath at 30 breaths per minute from time t0 to time t1, and once for the sigh at time t1. Approximately six seconds following the sigh, monitor A begins detecting cardiac artifacts without invalidating them. After five cardiac artifact detects the supposed respiration rate approached the heart rate and the circuitry began invalidating the breath detects for approximately six seconds. During this period monitor A stopped consistently detecting every cardiac artifact. This is because the amplitude of the artifact is just at the sensitivity of the breath detector. Very slight changes in artifact amplitude as the base line is approached, result in inconsistent breath detections so that the supposed breath rate falls below the average heart rate. This causes the cardiac artifact rejection circuit to stop invalidating the spurious breath detects, allowing some false detects to be treated as breaths during the time during which the signal returns to baseline. As the signal reaches the baseline, the respiratory detector sensitivity becomes just sensitive enough to consistently detect the next seven cardiac artifacts. At this time the cardiac artifact rejection circuit finally locks out the breath detections and the monitor begins measuring the apnea period, 40 seconds after it began.

Prior art monitor B compares a single breath detection interval with a single ECG detection interval. As with monitor A, breath detection sensitivity is just at the level which detects the 0.25 ohm cardiac artifact, resulting in inconsistent intervals between breaths. When these intervals are compared with the corresponding ECG intervals, there are large differences at times. When this occurs, the cardiac artifact is occasionally accepted as a valid breath. The result is that monitor B never reaches the 15 second apnea alarm time and no alarm occurs.

Prior art monitor C has no cardiac artifact circuitry. Every cardiac artifact greater than the sensitivity of the breath detector is assumed to be a breath. In this example, all artifacts were of sufficient amplitude to be incorrectly sensed as breaths. No apnea alarm sounded, since no cessation in breathing was detected.

Another manifestation of alarm failure results from switch errors and failures. Some attempts have been made to make alarm limit switch settings tamper resistant. One approach is to hide switch settings behind a trap door that is not easily opened. This approach makes it difficult to quickly review switches settings at a glance. This method also does not guarantee that the trap door has not been opened and switches changed.

Another approach is to sound an alarm if accessible switches are changed, while the unit is operating, without simultaneously pressing the reset button. This somewhat safeguards tampering by an anauthorized operator. This method and the rest of the prior art does not address alteration of switch settings while the unit is off. Apparatus is needed for detection and warning of unauthorized switch setting alteration.

Additionally, switches are prone to failure. Failure can be due to the user positioning a switch between two settings such that the contacts for both settings either short together or such that neither contact is closed. This may result in both settings being sensed or in neither setting being sensed. Failure can also be mechanical such that one or more switch position contacts are shorted together or are open and do not make contact. The result of such mechanical failure may provide misleading input to the circuitry. These particular switch settings may become undefined in meaning, such as rate or length of apnea period is unclear or unknown. Thus the patient being monitored may not be monitored with appropriate alarm limits, resulting in a dangerous condition. What is needed is a way to verify that switch contacts are neither shorted nor open and are mechanically reliable.

What is needed is a reliable monitor which can differentiate between actual breath signals and cardiac artifacts. Additionally a device is needed which has both tamper prevention features and fail-safe feature in case of problems, so that alerts are not delayed or missed.

SUMMARY OF THE INVENTION

Prior art problems with rejection of cardiac artifacts are ameliorated by a system employing two detectors. As the prior art has shown, no single detector can satisfactorily sense both breaths and artifacts accurately. Artifacts must be correctly detected and identified in order to properly disregard the artifacts while detecting breaths.

In the present invention, one detector senses in the normal range for breath detection. A second detector senses in the amplitude range of cardiac artifacts. By using input from two detectors designed for respective detection tasks, the system more clearly differentiates artifacts from actual breaths. Once artifacts are correctly identified, they are ignored and the system continues to search for actual breaths.

The present invention involves a medical monitor comprising: means for receiving a respiration signal indicative of breathing activity; a first detector means, logically connected to the means for receiving, for sensing a characteristic of the respiration signal and for producing a first event signal indicative of a breath; a second detector means, logically connected to the means for receiving, for sensing the characteristic of the respiration signal and for producing a second event signal indicative of a breath; and means for determining, based upon the first and second event signals, whether a breath occurred.

The invention includes two detectors, which are preferably set to different sensitivities. The first or basic detector is preferably a threshold detector. A second or dual detector is preferably a peak detector which is more sensitive than the first detector.

The characteristic is preferably impedance across patient electrodes. The sensitivity is preferably amplitude of impedance, but may be other characteristics selected by one skilled in the art, such as rate of change of impedance or peaks of impedance.

Although the illustrated embodiment employs electrodes and analyzes electrode impedance, one skilled in the art may use other forms of patient sensing. For example, a strain guage, stretch guage, or an induction coil may sense body breathing activity and generate a respiration signal. The present invention is then used to detect and reject cardiac artifacts, or other artifacts, in the respiration signal generated by other selected sensors.

Devices constructed according to the present invention preferably receive signals of artifact-producing body activity, such as ECG signals indicative of heart beat. The system is preferably programmed to analyze ECG signals indicative of the occurrence of the QRS complex of ECG, breath detects based upon thresholds, and breath detects based upon peaks.

In one form, the system detects a breath with the basic detector. It then inspects the previous peak detect. The interval since the preceding peak detects are found. The previous ECG detect is inspected and intervals since preceding ECG detects are found. The last peak interval is compared to the last ECG interval. If the intervals are generally equal, the current detect is rejected and not counted as a breath.

The present invention includes an alarm, preferably a sonalert, with a normal state of being on. The logic means, preferably a microprocessor, inhibits the alarm, while normal conditions are sensed, by timed inhibit pulses. If errors occur, pulses stop and the alarm is activated. If the system fails, the logic means is such that this line will not be pulsed, thereby sounding the alarm.

The present invention preferably includes means to store switch parameters. When the system is powered up, current settings are compared to the stored settings. If not generally identical, an alarm sounds. This prevents tampering with switches even if the unit is turned off.

The present invention preferably includes a means to check all switch contact positions of each alarm limit switch to verify that exactly one contact is closed. Additionally, the present invention preferably includes a means to check the reset switch to verify that it is not shorted.

DETAILED DESCRIPTION OF THE PREFERRED EMBODIMENT

Figure 4A:
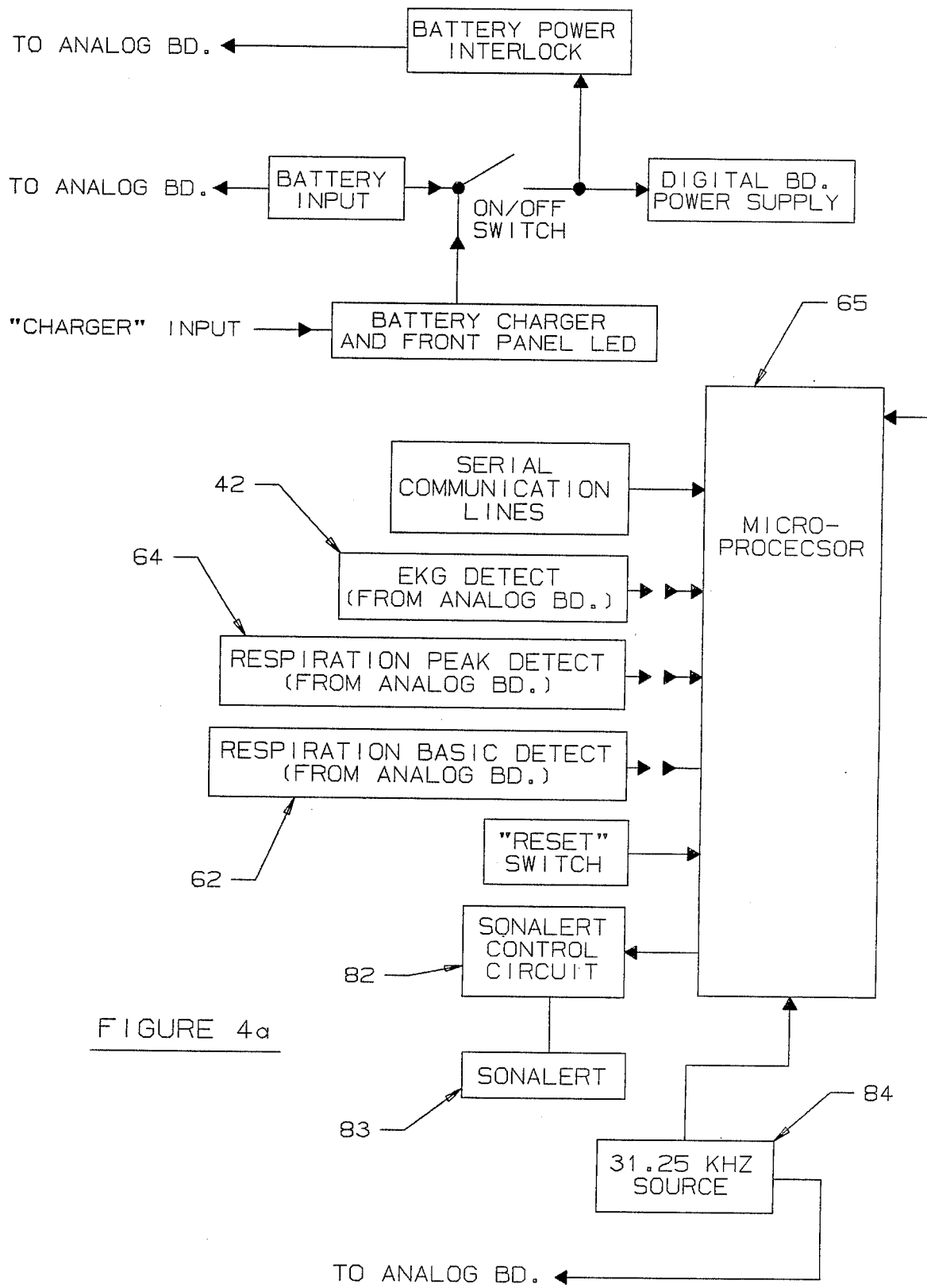
FIG. 4a and 4b are a block diagram of the digital circuit board of the monitor of FIG. 3.
Figure 4B:
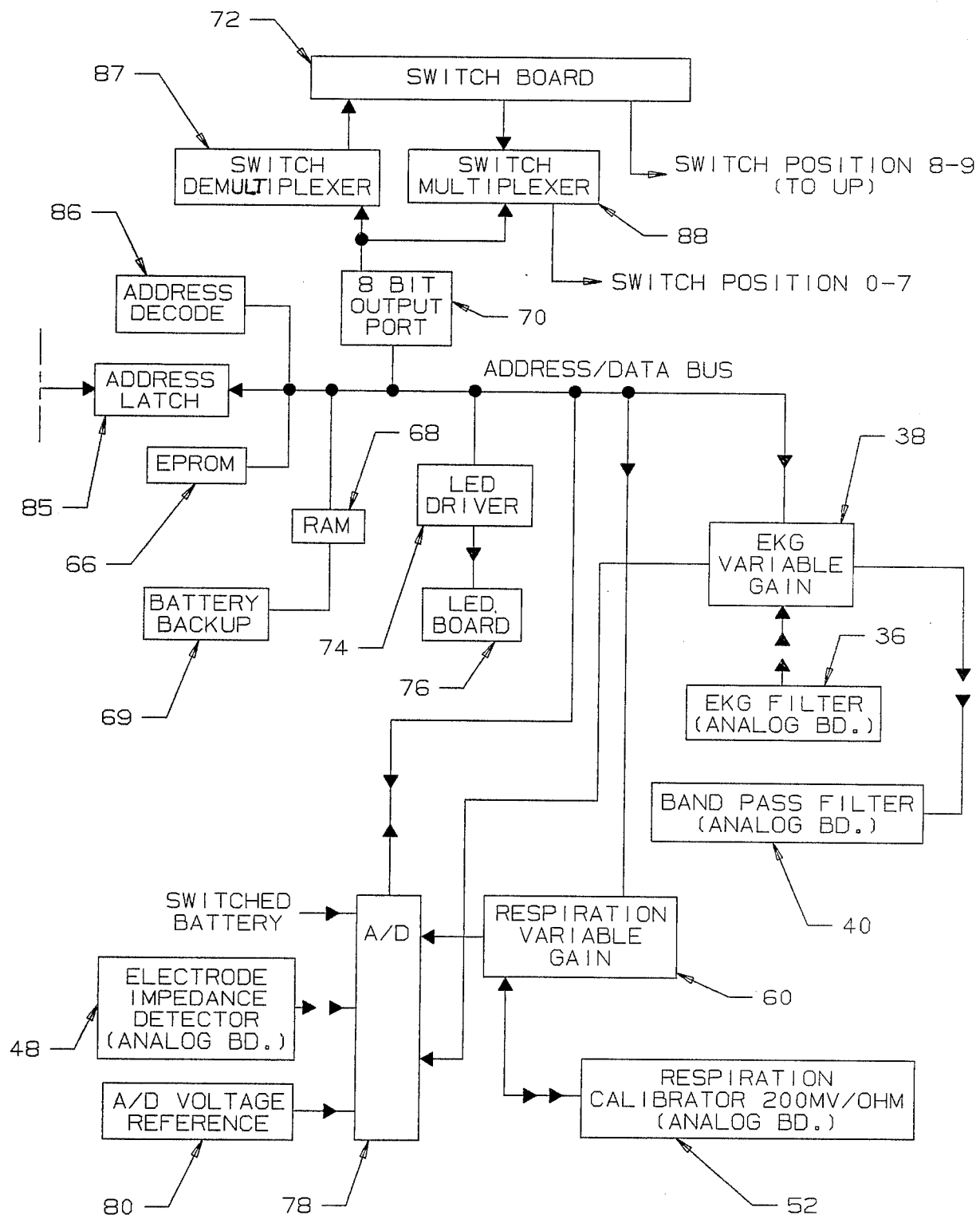

The embodiment illustrating the present invention is shown in FIGS. 3–5. The hardware of the embodiment is primarily described using FIGS. 3 and 4. The circuitry for embodying the invention may easily be built by one skilled in the art. Portions of the circuitry relating to certain elements of FIGS. 3 and 4 are shown in FIG. 5.

Electrical signals of a patient are monitored by using electrodes 10 mounted across the patient's chest. Signals from electrodes 10 are received through electrostatic discharge (ESD) protection circuit 12, which prevents static charge build-up from damaging circuitry.

A constant current source 14 drives the electrodes at 31.25 KHz in a square wave. With this contant current, any change of impedance across the electrodes 10 will generate a change in voltage, known herein as a respiration signal.

The varying voltage is picked up by differential amplifier 16. Differential amplifier simultaneously picks up the voltage generated by the patient's ECG signal. Both the varying voltage caused by impedance change and the ECG voltage are amplified by differential amplifier 16.

The ECG signal is extracted by filtering out the 31.25 KHz portion of the signal by ECG filter 18. The ECG signal is then modulated by the 31.25 KHz signal by modulator 19 and passed through isolation transformer 20 to the non-isolated section of the circuitry.

Similarly, the respiration signal from differential amplifier 16 already modulated at 31.25 KHz goes through isolation transformer 22 to the non-isolated section of the circuitry.

Power is obtained from non-isolated battery 24. The positive non-isolated power is regulated by positive supply 25. The power is modulated at 31.25 KHz from one MHz/31.25 KHz source 84 on the digital board (FIG. 4) through 31.25 KHz modulator 27 (FIG. 3), driving isolation power transformer 28. Negative non-isolated voltage is rectified by rectifier 29, providing the non-isolated negative supply 26.

Isolated supply voltages are generated through isolation power transformer 28. They are rectified by rectifiers 29, providing isolated positive and negative supplies 30.

The ECG signal is demodulated by ECG demodulator 31 and the 60 Hertz component is removed by 60 Hertz filter 32. The ECG signal is further filtered and amplified by calibration amplifier 34 and ECG filter 35 to produce 200 millivolts output per millivolt of ECG input at the recorder output 36 and pneumogram output 37, such as an Oxford recorder.

The signal is passed to the digital board (see FIG. 4) where microprocessor-controlled ECG variable gain 38 further amplifies the signal according to the set sensitivity. The signal returns to the analog board (see FIG. 3) where the ECG is filtered by bandpass filter 40 and is threshold-detected by ECG detector 42. The detected ECG signal, in the form of a short pulse, travels to the digital board as a port input to microprocessor 65 (FIG. 4).

The DC component of the respiratory signal is detected by respiration demodulator 46 (FIG. 3). The respiration signal is conditioned by electrode impedance detector 48. The impedance signal then travels to the digital board (see FIG. 4) where it is sampled by A/D 78, which assures that the base impedance signal is within acceptable bounds. Loose lead conditions are determined this way as well as when electrode impedance is getting high, thereby indicating that electrodes are aging and should be replaced.

The DC component of the base impedance signal is removed by respiration filter 50, resulting in a respiratory signal indicative of changing impedance. This signal is amplified and calibrated to 200 millivolts output per ohm change in input impedance at calibration amplifier 52.

The resulting signal is sent to various standard output devices, including as recorder output 54 and pneumogram output 56, such as an Oxford recorder. This is commonly used to produce a 12 or 24 hour tape recording of heart and respiration activity.

The respiration signal goes through respiration clamp circuit 58, which is used to shorten the RC time constants when large motions or loose lead conditions occur. The signal passes to respiration variable gain 60 on the digital board, controlled by microprocessor 65 according to the sensitivity set on the switch board 72 (FIG. 4). The amplified signal then returns to the analog board to respiration basic detector 62 (FIG. 3) and to respiration peak detector 64, which is a positive and negative peak detector in this embodiment. The output of detectors 62 and 64 go to the digital board to ports of microprocessor 65.

The basic respiration detector 62, in the illustrated embodiment, is designed to go high between the respiration minimum and maximum and to go low between the respiration maximum and minimum. It is sensitive to 0.2 ohm from 15 to 100 breaths per minute, in this example.

Figure 5A:
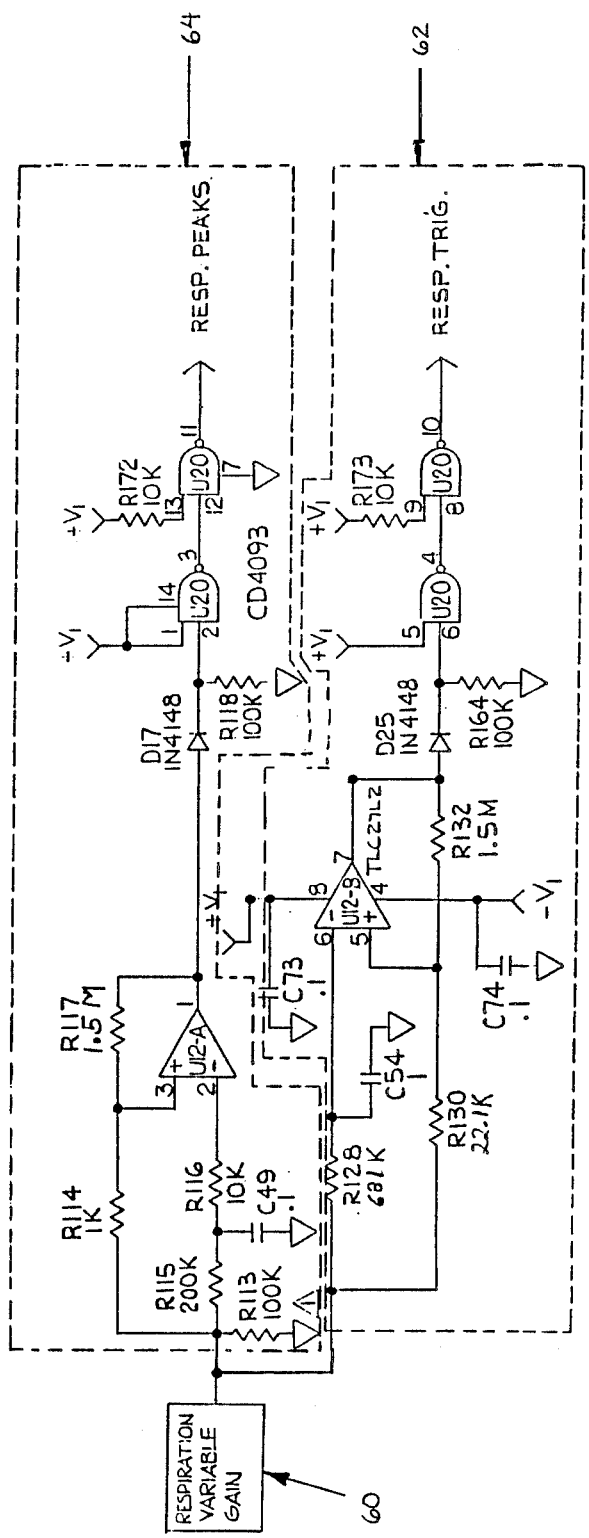
FIGS. 5a–c and 5Ba–Bf are a schematic drawing of the circuitry of portions of the boards of FIGS. 3 and 4.

The configuration of the basic respiration detector 62 is a peak or slope change detector with hysteresis. In FIG. 5a the input signal through resistor R130 (22.1 Kohm) is compared to a delayed signal due to resistor R128 (681 Kohm) and capacitor C54 (1 microfarad) by comparator U12-B. Resistors R130 and R132 (1.5 Mohm) provide hysteresis. While the input signal is increasing, it is greater in amplitude than the delayed signal. When the signal is decreasing, the delayed signal is greater. When the amplitude difference is great enough to overcome the hysteresis generated by feedback through resistor R132, the output of the comparator U12-B changes state. When the signal increases again, it becomes greater in amplitude than the delayed signal and, after overcoming the hysteresis voltage, the output of comparator U12-B changes state once again.

Diode D25 (IN4148) and resistor R164 (100 Kohm) clamp the comparator output to $+V_1$ and ground. Schmitt trigger U20 buffers the comparator U12-B output. The output of Schmitt trigger U20 goes to the digital board and is sampled by microprocessor 65.

Peak detector 64 makes a positive to negative transition for every positive peak. For a negative respiration peak, detector 64 makes a negative to positive transition.

Resistor R115 (200 Kohm) and capacitor C49 (0.1 f) form a phase delay network that delays the respiration input to one leg of comparator U12-A. Resistors R114 (1 Kohm) and R117 (1.5 Mohm) provide comparator feedback and are trip point resistors.

Diode D17 (IN4148) and resistor R118 (100 Kohm) clamp output of comparator U12-A to $+V_1$ and ground. Schmitt trigger U20 buffers output of comparator U12-A to the digital board. This output is sampled by microprocessor 65 to determine when positive and negative peaks of respiration have occurred.

In this embodiment microprocessor 65 (FIGS. 4 and 5b) is a Hitachi 6303 8-bit device with 128 bytes of internal RAM, with 13 I/O lines and a 16 bit timer. At power up microprocessor 65 is reset on the rising edge of the reset line. Microprocessor 65 latches port P20-P22 to determine the start-up mode. After the reset goes high, microprocessor 65 begins operation, and looks to ports P20-P22 for input. The software also utilizes the opcode trap of microprocessor 65 to assure that every instruction executed is valid.

Microprocessor 65 receives a 1 MHz clock frequency. It generates a 250 KHz system clock. The microprocessor 65 multiplexed data/address bus is separated by address latch 85 to form the system bus. The bus of microprocessor 65 is attached to EPROM 66, which contains all stored programs embodying the decision process outlined below. Illustrated EPROM 66 is an 8K by 8 CMOS EPROM.

Also on the bus is RAM 68, which is, in this example, a 2K by 8 CMOS RAM. Battery power is provided by battery back-up 69 so that RAM 68 is non-volatile memory. Memory is retained when the monitor is turned off. Switch settings are stored in RAM 68.

Figure 5B:
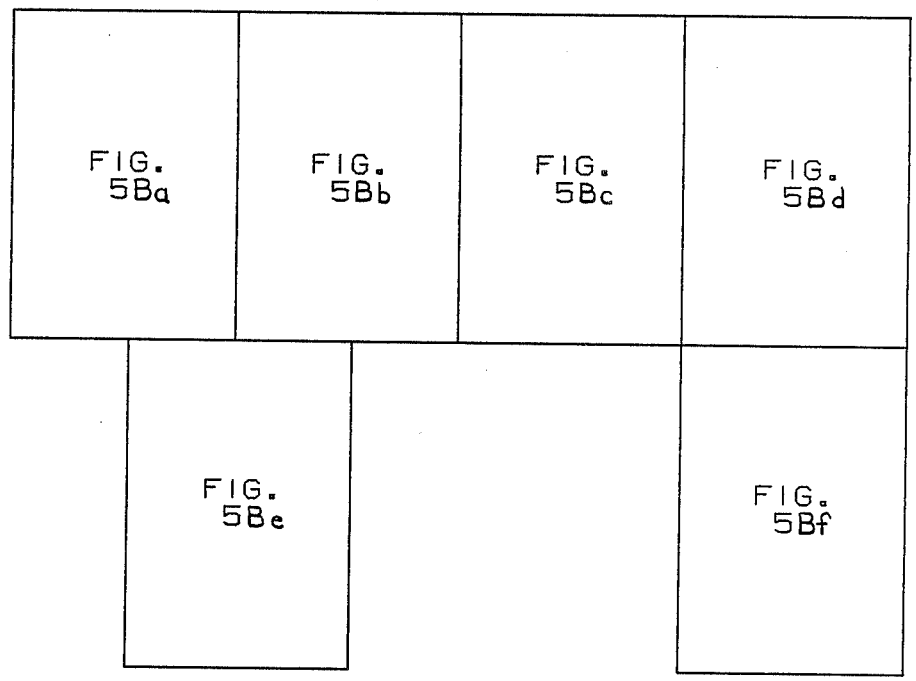
Figure 5B:
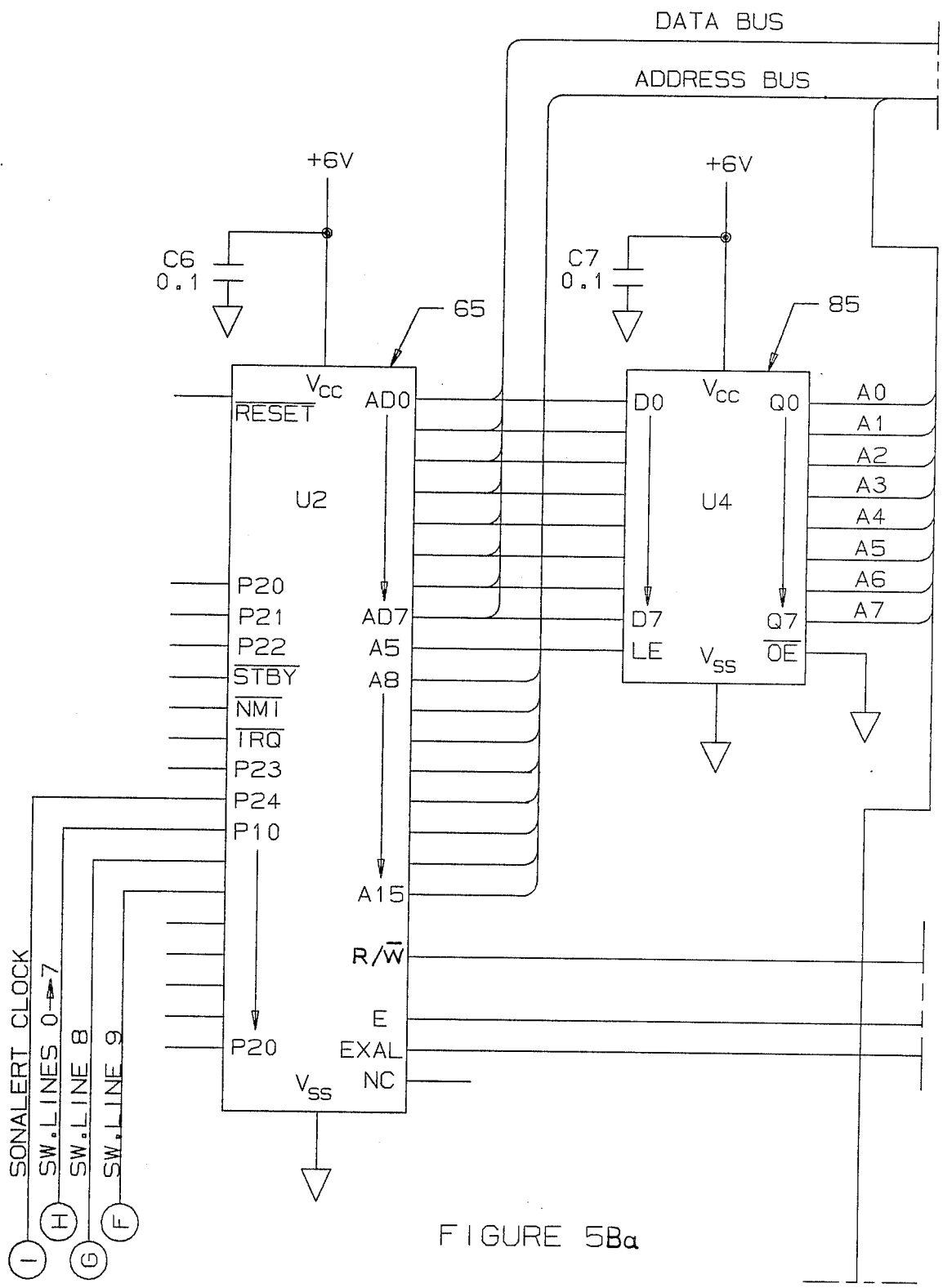
Figure 5B:
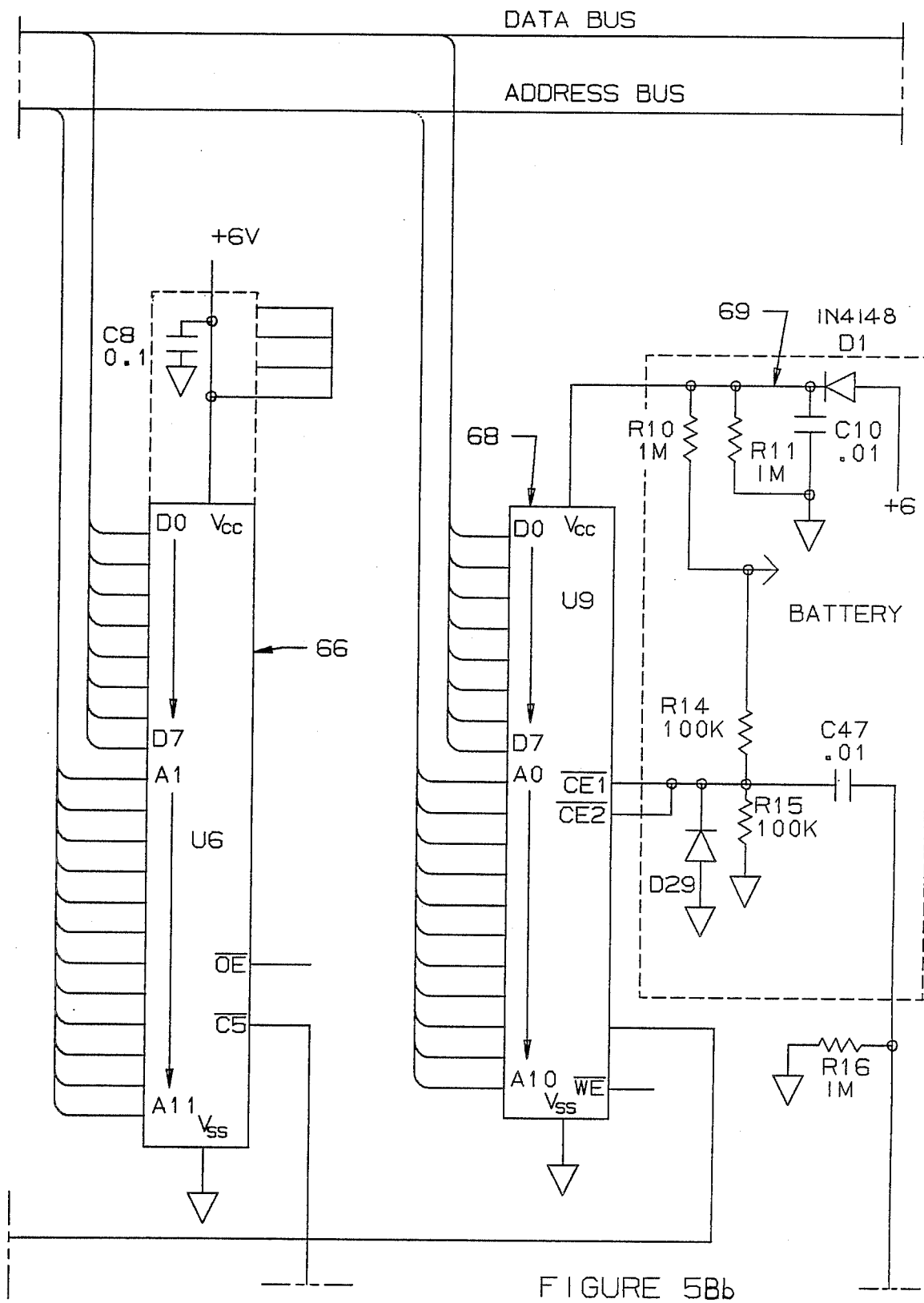
Figure 5B:
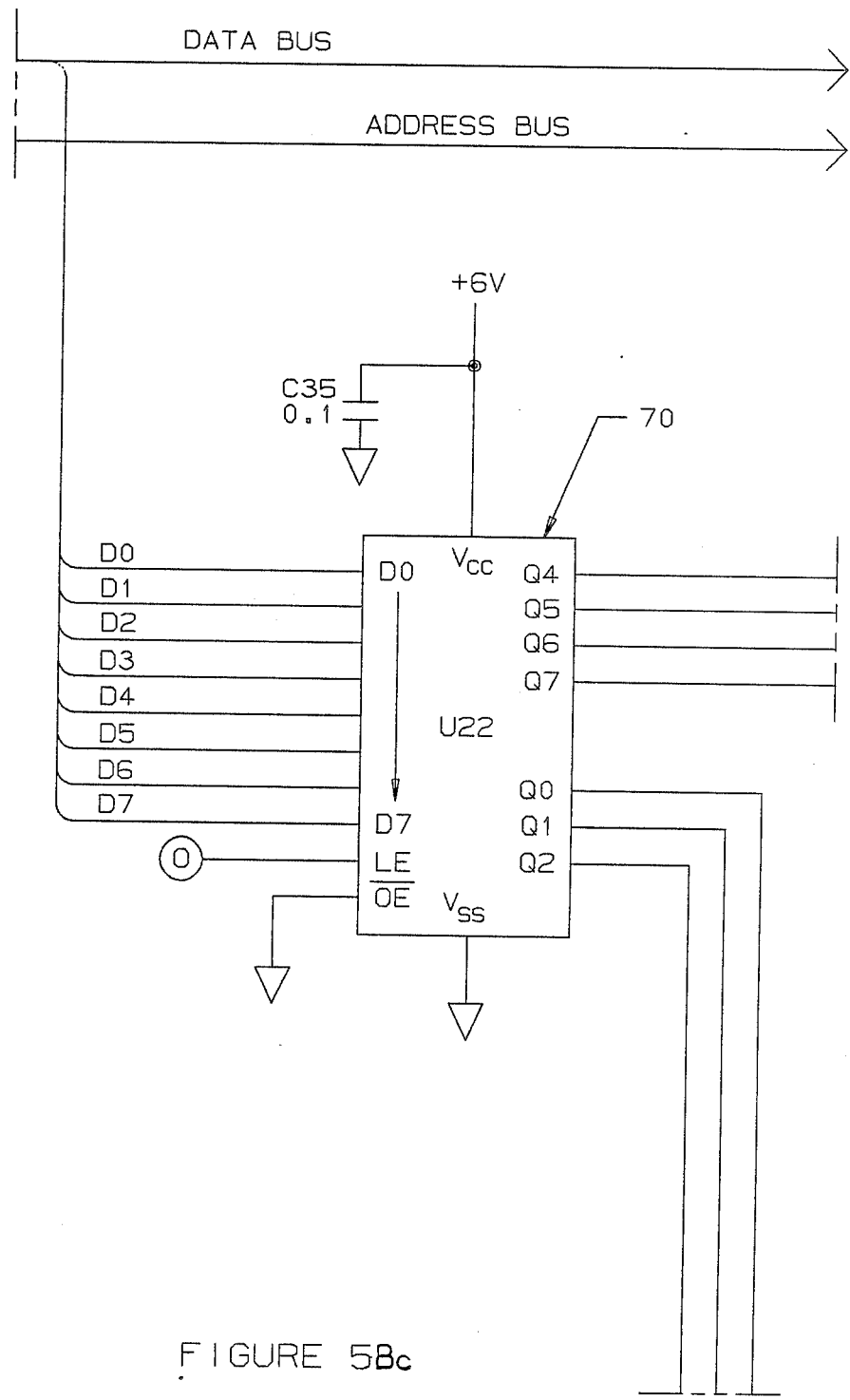
Figure 5B:
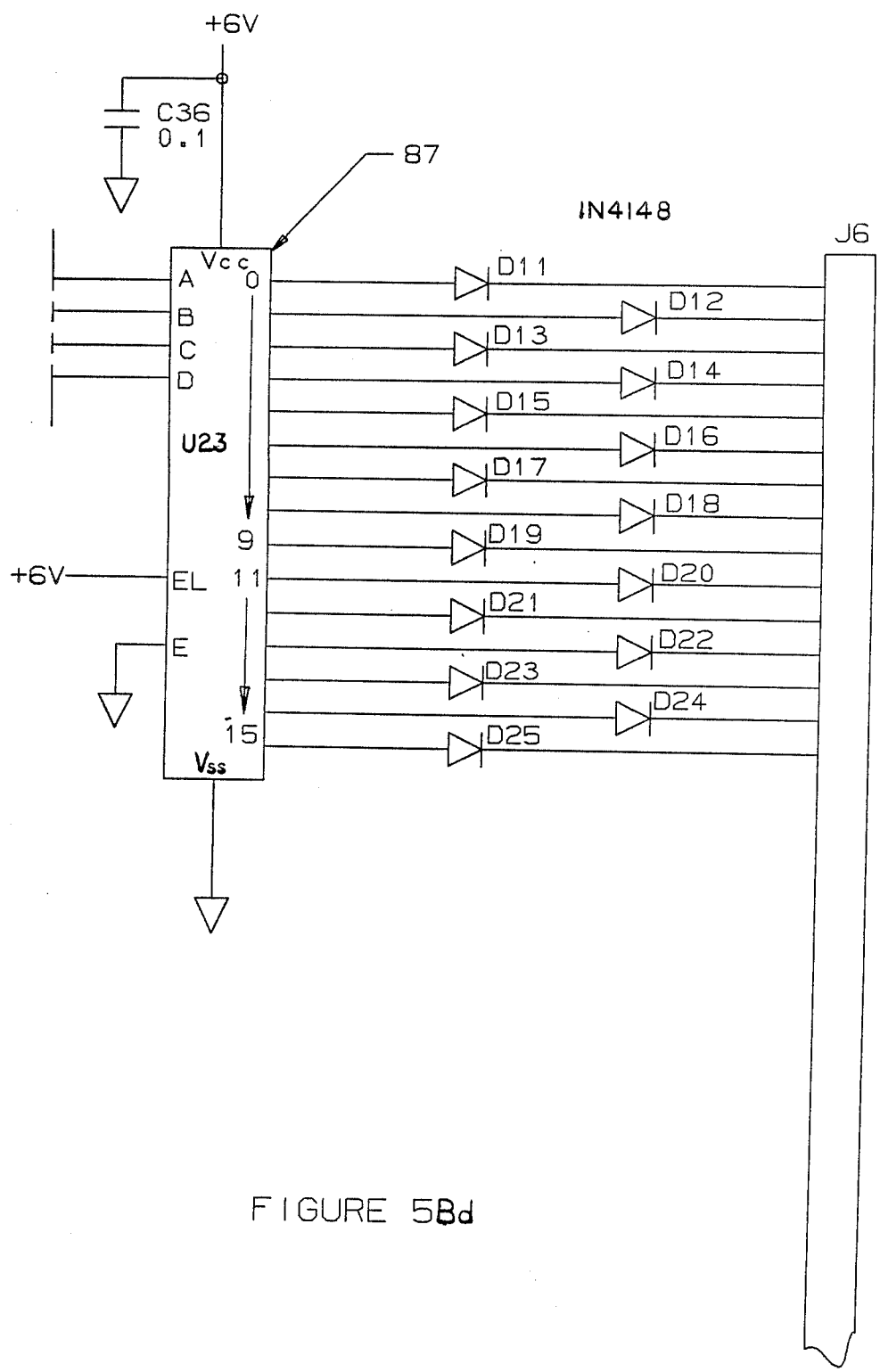
Figure 5B:
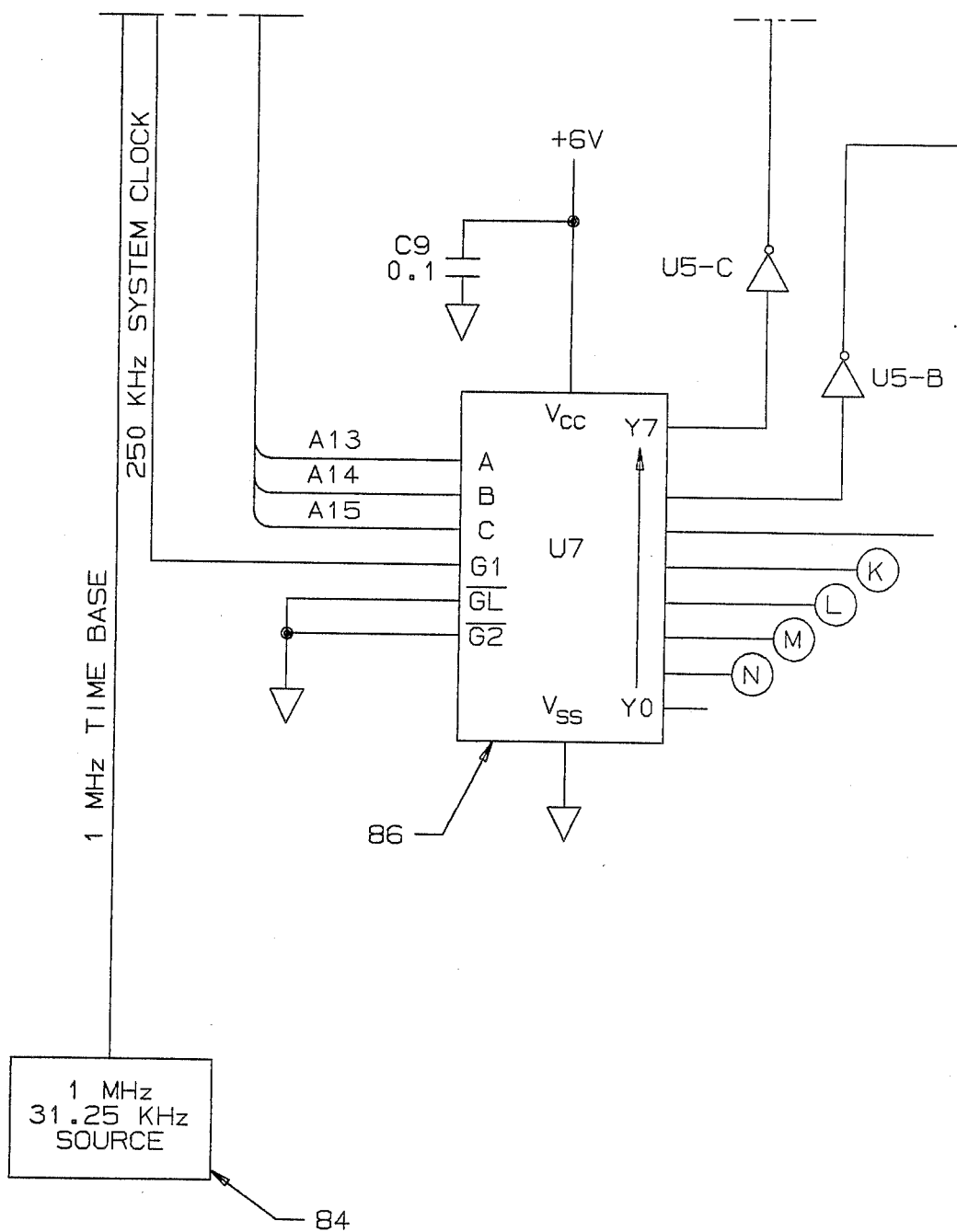
Figure 5B:
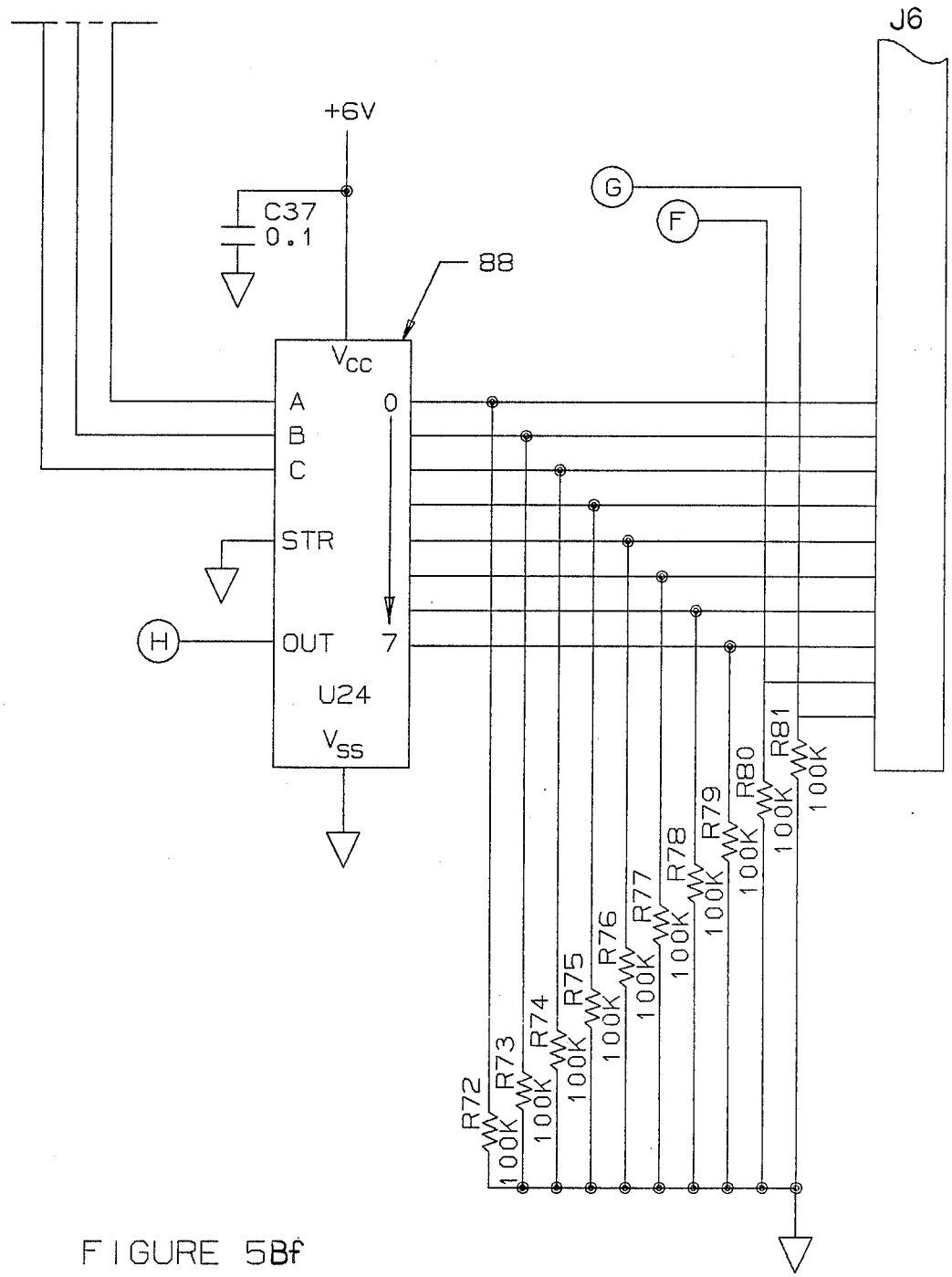
Figure 5C:
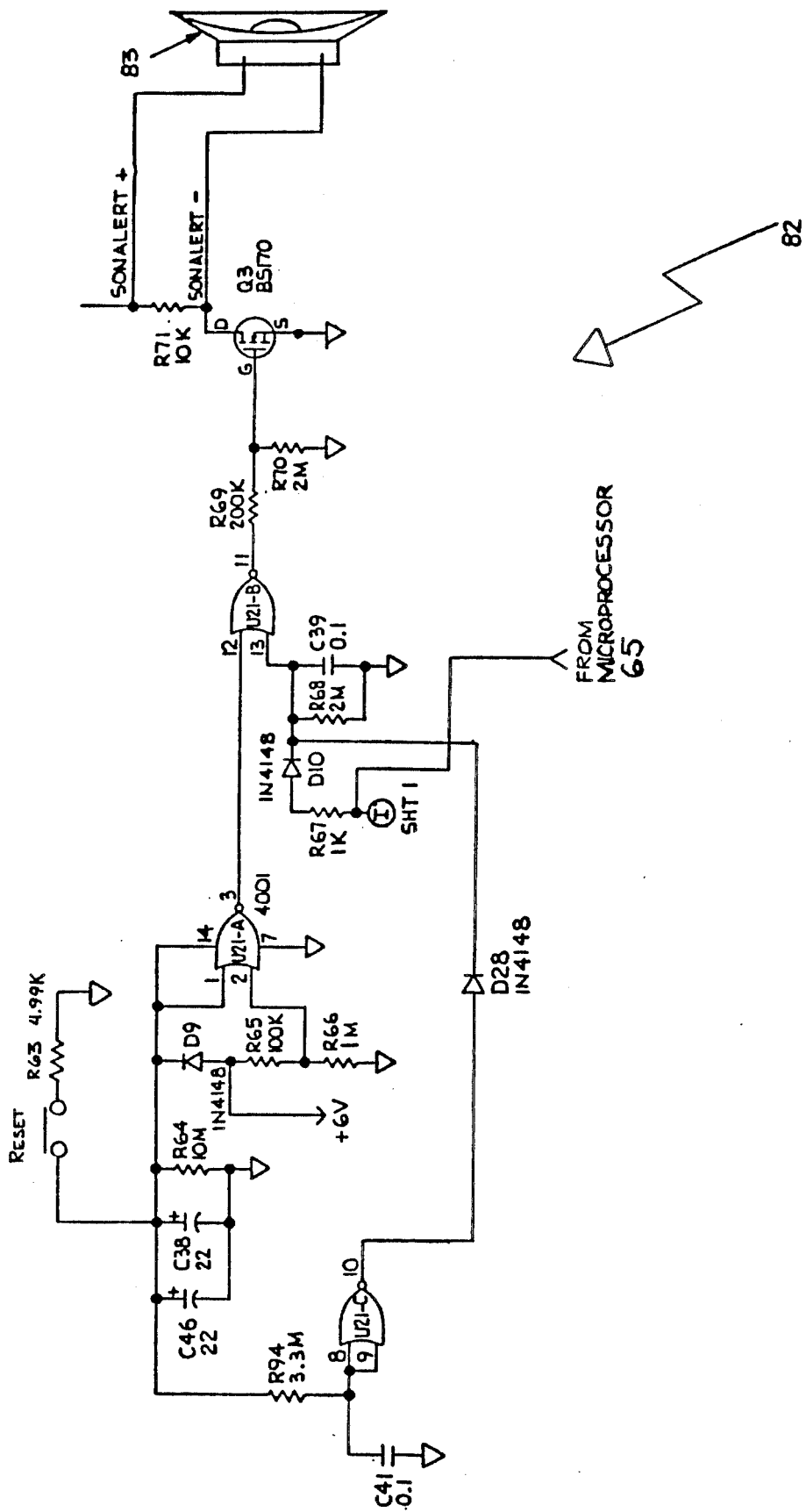

On the bus is an 8-bit output port 70 used by microprocessor 65 to control switch demultiplexer 87 and switch multiplexer 88. Both switch demultiplexer 87 and switch multiplexer 88 are used to read the switch settings from switch board 72, which contains manually-settable switches. The circuit is shown in FIG. 5b. Microprocessor 65, reading instructions from EPROM 66, selects a switch to read. The particular switch common is selected by writing a code to the 8-bit output port 70. This code is then decoded by the switch demultiplexer 87 and the desired switch's common is activated. Microprocessor 65 then reads the individual switch lines 0-7 by again writing a code to the 8-bit output port 70 which controls the switch multiplexer 88. Microprocessor 65 then directly reads lines 8 and 9 to determine the state of these lines. By changing the code written to the switch demultiplexer 87, microprocessor 65 is able to read all the switches on switch board 72.

Microprocessor 65 stores the values of the switches in RAM 68. Upon power-up, the switches are read and compared to their stored values. If these values are not equivalent, an alarm is sounded.

Switch board 72 contains banks of switches used for setting parameters. Each bank of switches has common 0-9 outputs. Only one bank is driven at a time, so only the setting of the 0-9 switch of that bank will be seen by microprocessor 65.

Switch alarms will occur if switches of switch board 72 have been changed without authorization or if there is a hardware failure, such as an open switch or a shorted switch.

If switch settings on switch board 72 are altered while the unit is powered off, microprocessor 65 will discover the change by examining the stored settings in RAM 68 and comparing to the current switch settings during power-up. If switches have been altered microprocessor 65 causes an alarm to be issued.

Also on the bus is LED driver 74, which drives the display of LED board 76. LED board 76 provides visual indication of alarms and status.

Analog-to-digital converter A/D 78 is connected to the bus and receives signals from electrode impedance detector 48, ECG variable gain 38, and respiration variable gain 60. A/D 78 in this example is an ADC0809 8-bit, 8-channel device. A/D 78 monitors battery level, electrode impedance level, respiration signal amplitudes and positive ECG amplitude.

A/D voltage reference 80 sets voltage at 4.5 V in this example.

Sonalert control circuit 82 (FIG. 5c) sets sonalert 83 in an on state. Microprocessor 65 must send inhibit pulses to sonalert control circuit 82 to keep the alarm off. The sonalert 83 is turned on by raising the gate of FET Q3 (BS170) to $+V_1$ level. The gate of FET Q3 is controlled by logic gate U21-B (HEF 4001).

At power-on, gate U21-B receives a zero on one leg and a one on the other leg. This holds the sonalert 83 off. When microprocessor 65 comes up, inhibit pulses are dumped into a charge reservoir consisting of diode D10 (IN4148), resistor R68 (2 Mohm), and capacitor C39 (0.1 f). If the inhibit pulses cease, the charge reservoir bleeds off via capacitor C39 and resistor 68, and sonalert 83 sounds.

If monitor power is turned off without pressing the reset switch, the charge on capacitors C46 (22 microfarad) and C38 (22 microfarad) holds gate U21 on and causes the sonalert 83 to sound. If the reset switch is held, capacitors C46 and C38 discharge through resistors R63 and R64 and the sonalert is not heard.

Using the inputs described, microprocessor 65 is programmed to issue alerts at predetermined events, such as if breath rate is slower than the slow-breath switch setting or if an apnea is longer than the apnea-delay switch setting.

The embodiment described is basically a motion detector. With each breath, impedance across electrodes 10 changes. As the lungs fill with air, the chest expands. The electrodes 10 become further spaced, increasing impedance.

The signal indicating motion of a breath is analyzed in the manner discussed below. The analysis is performed in programs loaded in EPROM 66 and controlled by microprocessor 65. One of ordinary skill in the art may program microprocessor 65 to perform the following procedures.

The present invention employs two detectors for detecting breath in a respiratory signal. In the illustrated embodiment they are respiration basic detector 62 and respiration peak detector 64. In this embodiment basic detector 62 is a threshold detector which triggers on the downward slope of the respiratory signal waveform. One skilled in the art may employ various detectors in its place. Respiration peak detector 64, although a peak detector in this embodiment, may be any other type of detector selected by one skilled in the art. In this embodiment peak detector 64 triggers on peaks by switching in one direction on a positive peak in the respiratory signal and switching in the other direction on a negative peak.

Of course, the dual detectors of the present invention may be embodied in many other forms. For example, both detectors may be embodied in a program in microprocessor 65. Input from respiration variable gain 60, in this alternate embodiment, is sampled continually and converted to digital values representing the sampled analog values. Two software detectors are employed. In one example the digital values are then analyzed for a basic breath detect and a peak breath detect. These are preferably done at different sensitivities. For example, they sense different signal amplitudes.

Respiration peak detector 64 is set at a sensitivity greater than that of respiration basic detector 62. That is, respiration peak detector 64 will sense smaller changes in impedance than will respiration basic detector 62. Because of this more sensitive detection, respiration peak detector 64 will detect a breath every time respiration basic detector 62 detects a breath. When a breath is below the threshold of respiration basic detector 62, respiration peak detector 64 may still detect the breath.

Figure 6:
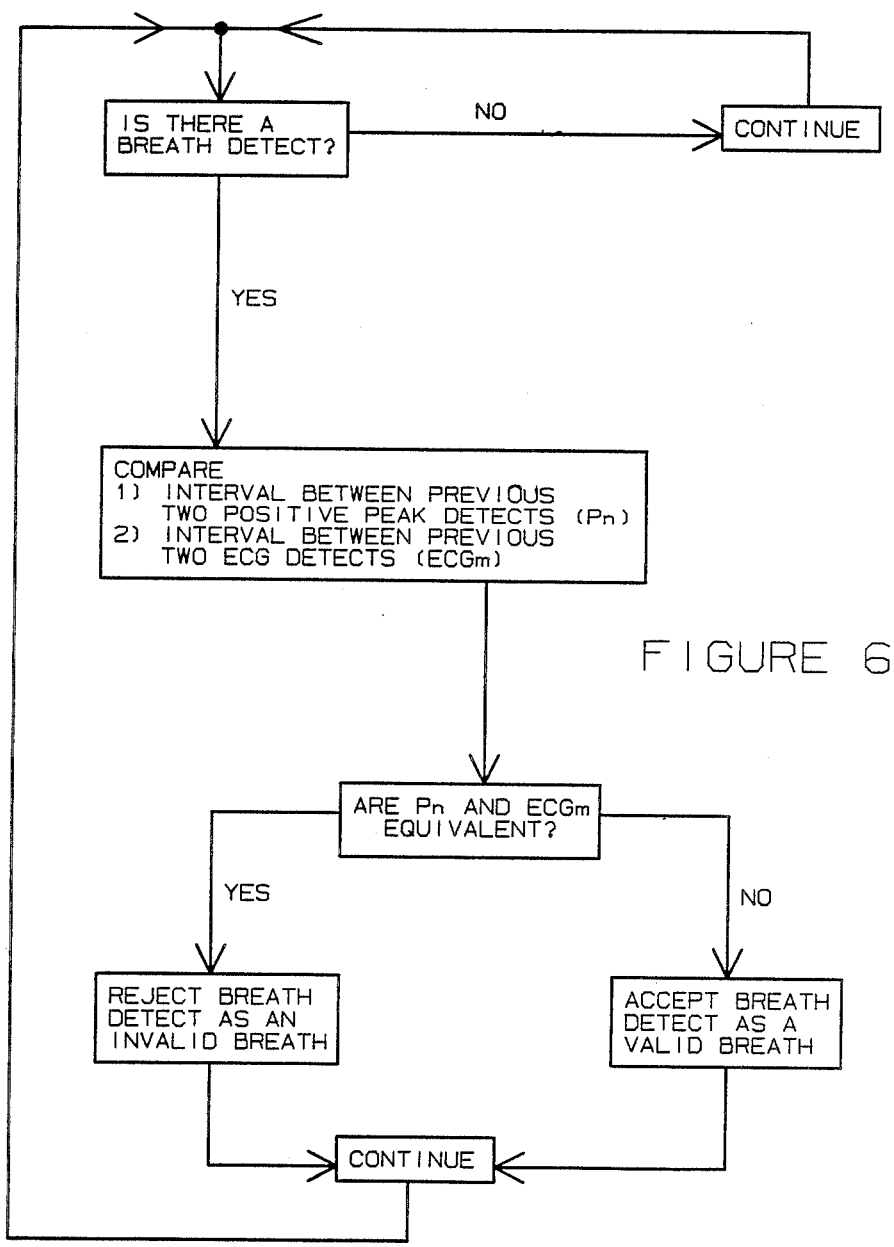
FIG. 6 is a flow chart illustrating the programming of the microprocessor of the embodiment of FIGS. 3–5, according to the present invention.

In the illustrated embodiment, the programming of microprocessor 65 is shown in the flow chart of FIG. 6. First the system looks for a breath detect. If there is none, the looking continues. When a breath is found, a comparison is made of the interval between the two previous positive peaks found by respiration peak detector 64 and the interval between the previous two ECG detects by ECG detector 42. If the intervals are equivalent it is assumed that the breath detect is a cardiac artifact. The breath detect is invalidated and not counted as a breath.

Figure 1A:
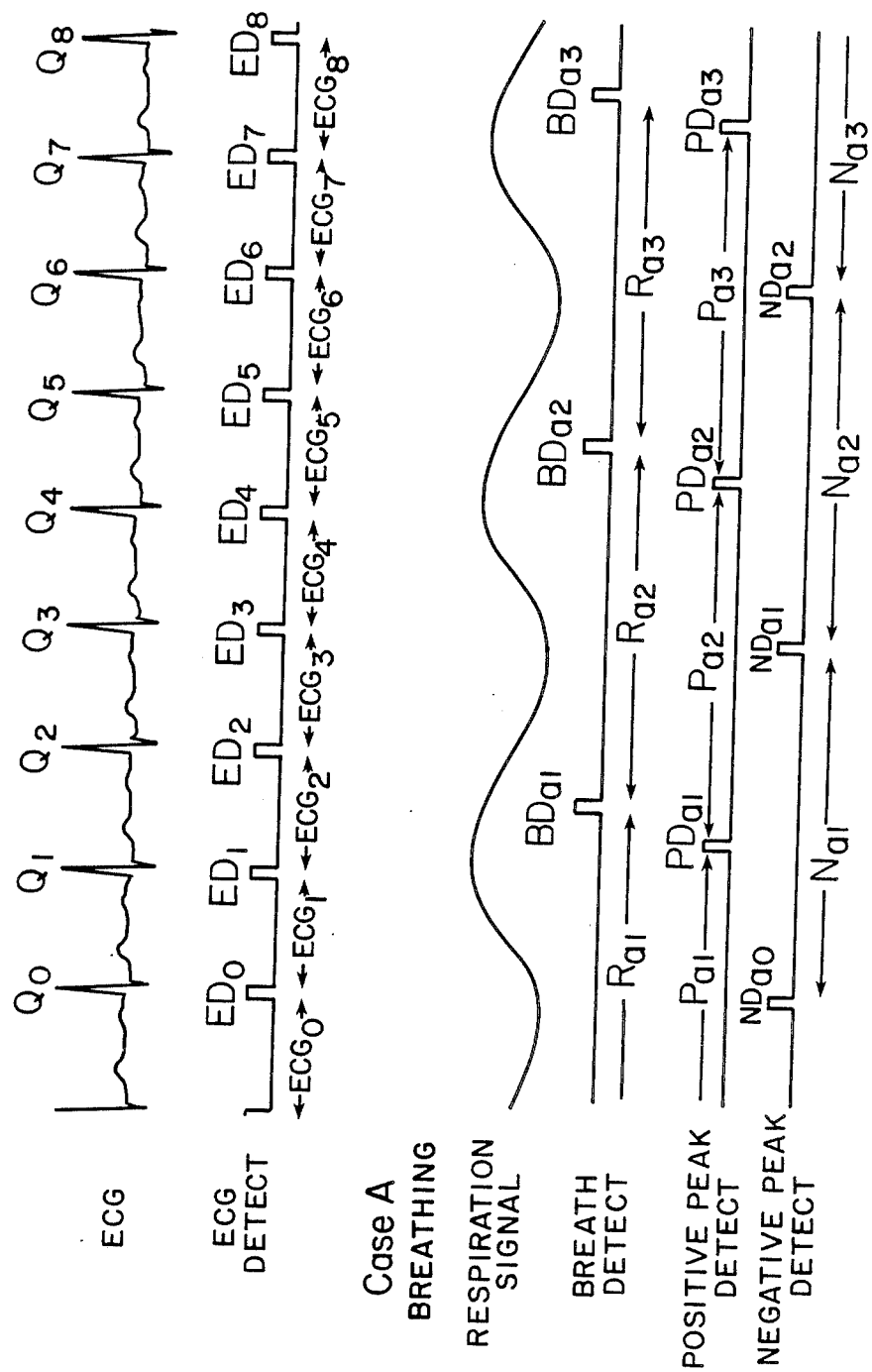
FIG. 1a, 1b and 1c depict a chart of electrical signals and detected events portrayed on a horizontal time line.

Using Case A of FIG. 1a as an illustration, time intervals between ECG detects, $ECG_0$-$ECG_8$, are stored in microprocessor 65 internal storage. In addition, time intervals between breath detects, $R_{a1}$-$R_{a3}$; time intervals between positive peak detects, $P_{a1}$-$P_{a3}$; and time intervals between negative peak detects $N_{a1}$-$N_{a3}$ are stored in microprocessor 65 internal storage. Instead of using the breath detect intervals $R_{a1}$, $R_{a2}$ and $R_{a3}$ to determine average breath rate, the present invention uses intervals $P_{a1}$, $P_{a2}$ and $P_{a3}$. In Case A the average breath interval is not equal to the average heart interval. In addition the interval $P_{a1}$ is not equal to the previous ECG interval $ECG_1$. Consequently breath detect $BD_{a1}$ is accepted as a valid breath by the monitor. In this case, the response is the same as if only a single breath detector were used as described in prior art.

All tests are for values within a tolerance factor. The tolerance factor may be a fixed time or a variable time based on how long the interval is. In the illustrated embodiment it is a flexible tolerance which increases with the actual length of the interval.

Large cardiac artifacts are illustrated in Case B of FIG. 1. Each breath detect $BD_{b1}$-$BD_{b8}$ has a corresponding positive peak $PD_{b1}$-$PD_{b8}$, with intervals $P_{b1}$-$P_{b8}$. For breath detect $BD_{b1}$, comparison of interval $P_{b1}$ with $ECG_1$ shows equivalence, so the detect is rejected. Similarly all other intervals $P_{bj}$ are equivalent to $ECG_i$, so all detects in Case B would be rejected.

Figure 1B:
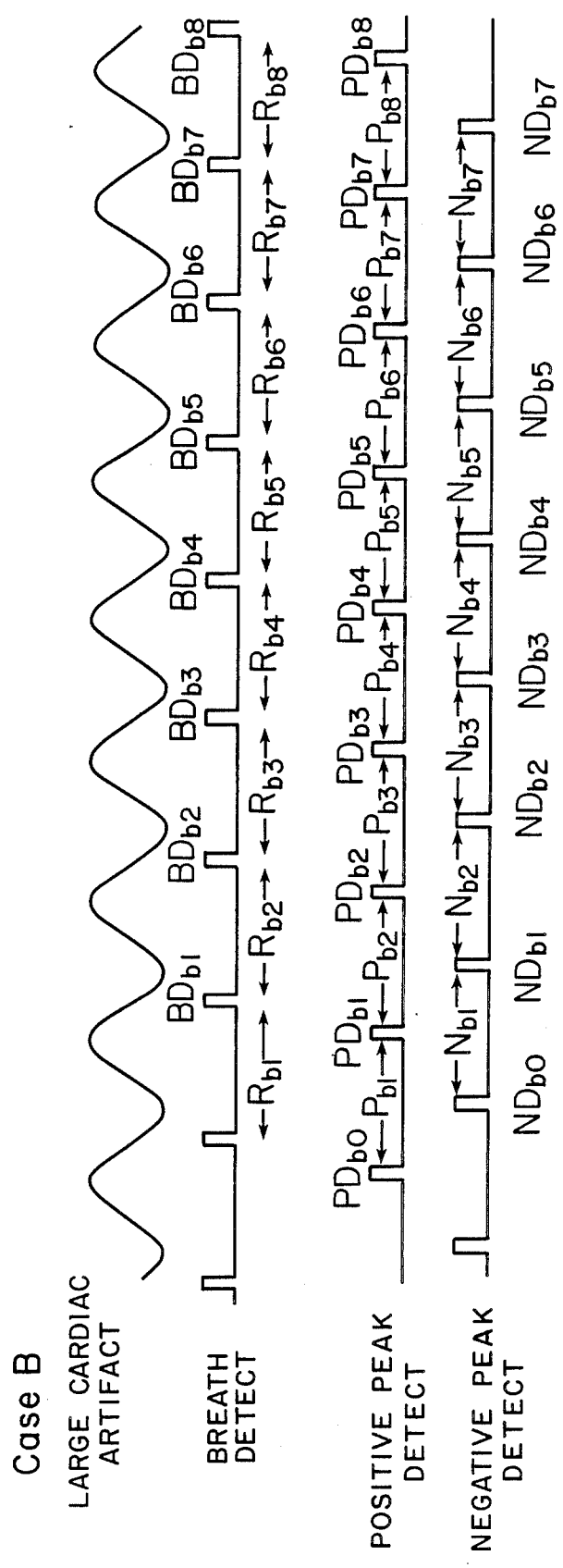
Figure 1C:
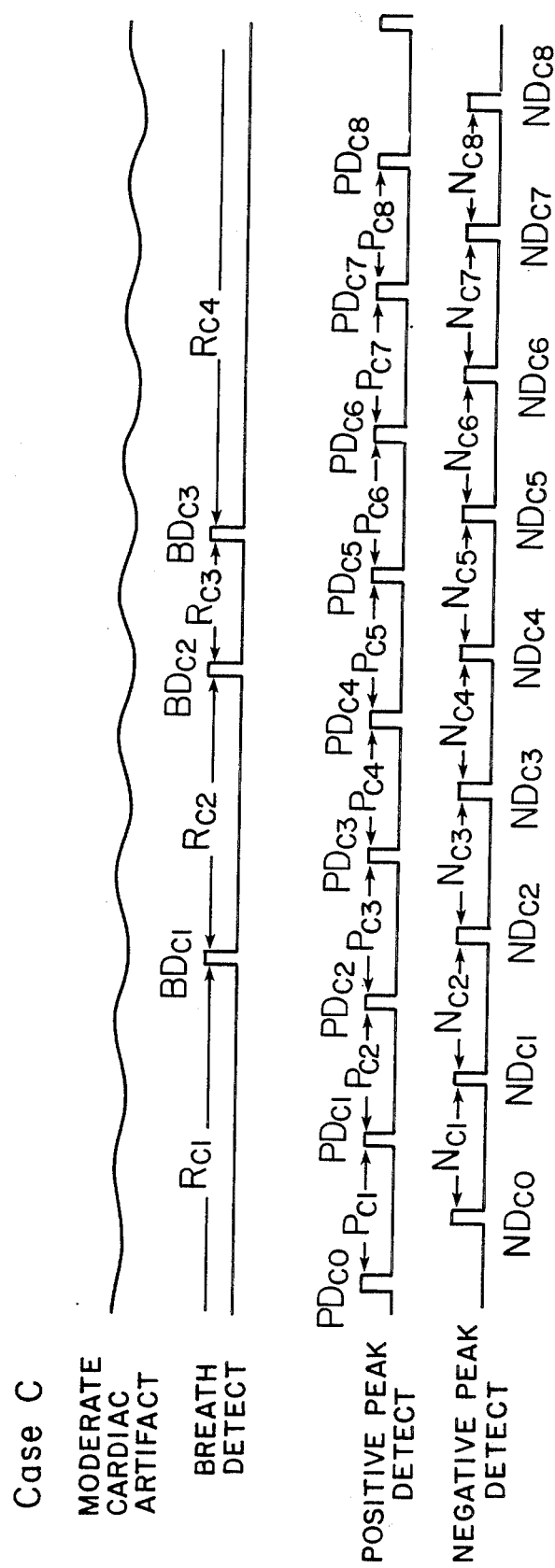

Case C of FIG. 1c illustrates a moderate cardiac artifact. This is of the type hardest for prior art monitors to reject. Following breath detect $BD_{c1}$, instead of using interval $R_{c1}$ to compare with interval $ECG_1$, the system of the present invention uses respiration peak detector 64 to find the previous positive peak detect $PD_{c2}$, which defines interval $P_{c2}$. Since interval $P_{c2}$ is equivalent to $ECG_1$, the breath detect is rejected. Likewise, following breath detect $BD_{c2}$, a comparison is made between intervals $P_{c4}$ and $ECG_3$. Since equivalence is found, detect $BD_{c2}$ is also rejected. For breath detect $BD_{c3}$, interval $P_{c5}$ is compared with interval $ECG_4$ and the breath detect is rejected.

Because the respiration peak detector 64 is more sensitive than the respiration basic detector 62, regardless of the amplitude of the cardiac artifact, the artifact will be rejected quickly and accurately.

This invention may be practiced by making comparisons between previous ECG interval and peak detect intervals, by comparing the last several ECG intervals with the last several peak detect intervals, or by comparing the average ECG detector rate with the average peak detector rate.

An alternative embodiment additionally measures intervals using negative peaks, such as $N_m$ in FIGS. 1a-c. Depending upon electrode configuration, heart rate, and change in heart rate, negative peaks may be more reliable and may be selected by the system. In this case the process would have the additional step of comparing the interval between the previous two negative peak detects interval $N_m$ and the interval between the previous two ECG detects $ECG_i$.

The sytem tests for either of the following conditions: (1) are intervals $P_j$ and $ECG_i$ equivalent or (2) are intervals $N_m$ and $ECG_i$ equivalent. If either interval comparison is equivalent, then the detect is rejected as an invalid breath detect. If neither interval comparison is equivalent, then the detect is accepted as a valid breath detect.

If the system determines that the detect was of a cardiac artifact, no signal indicative of a breath is issued. The sytem continues to receive detects from respiration basic detector 62, respiration dual detector 64, and ECG detector 42.

The system is continually determining the time since the last validated breath detected. An apnea interval is set by the user, usually the physician prescribing the device, on switches of switch board 72. This value is stored in RAM 68 and microprocessor 65. Using internal clocking, the system issues an alarm signal to alarm control circuit 82 if the apnea interval is reached without detecting a validated breath.

Figure 2:
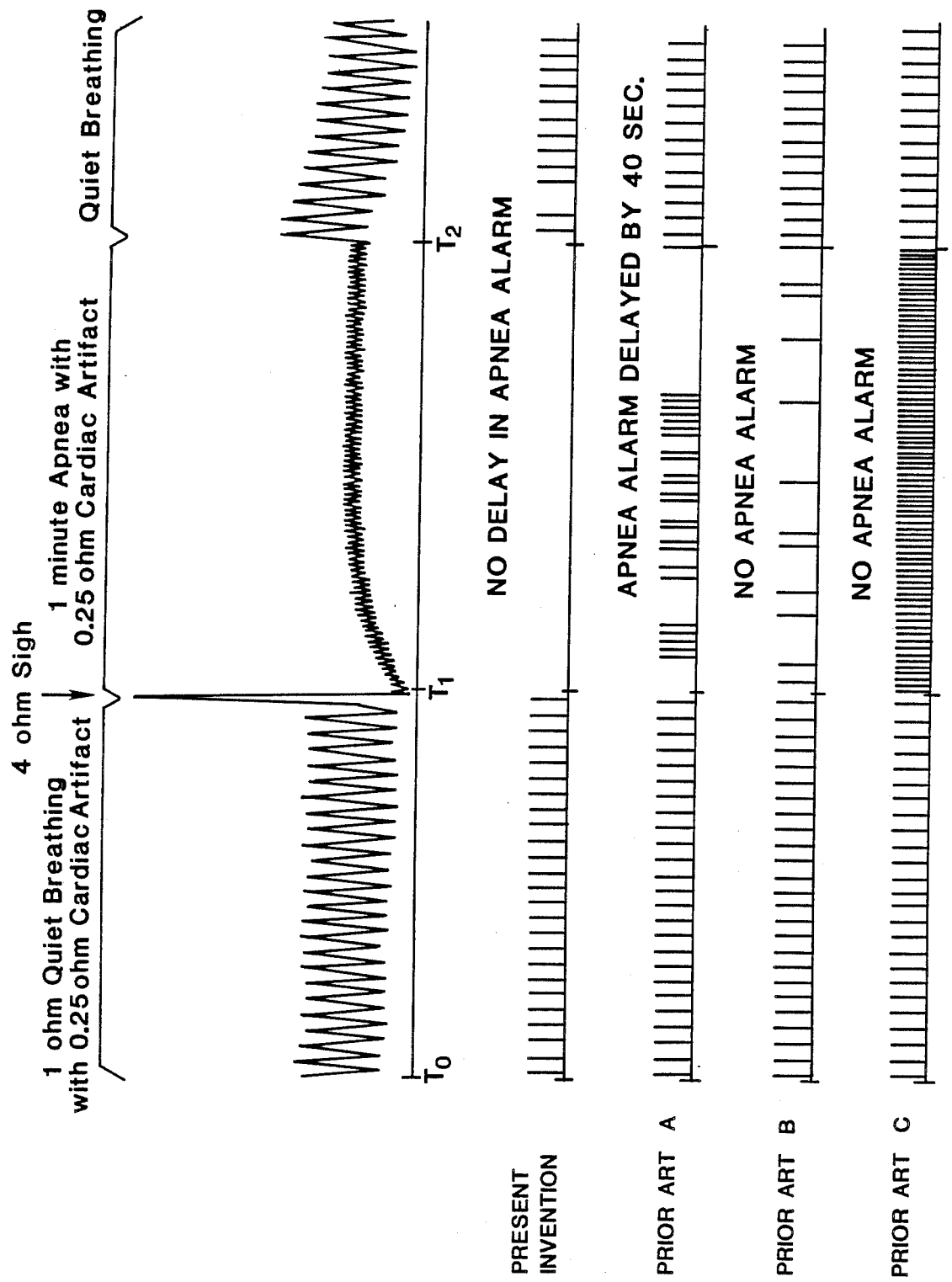
FIG. 2 is a chart along a horizontal time line illustrating performance of various prior art monitors and a monitor constructed according to the present invention monitoring an apnea with cardiac artifacts.
Figure 3A:
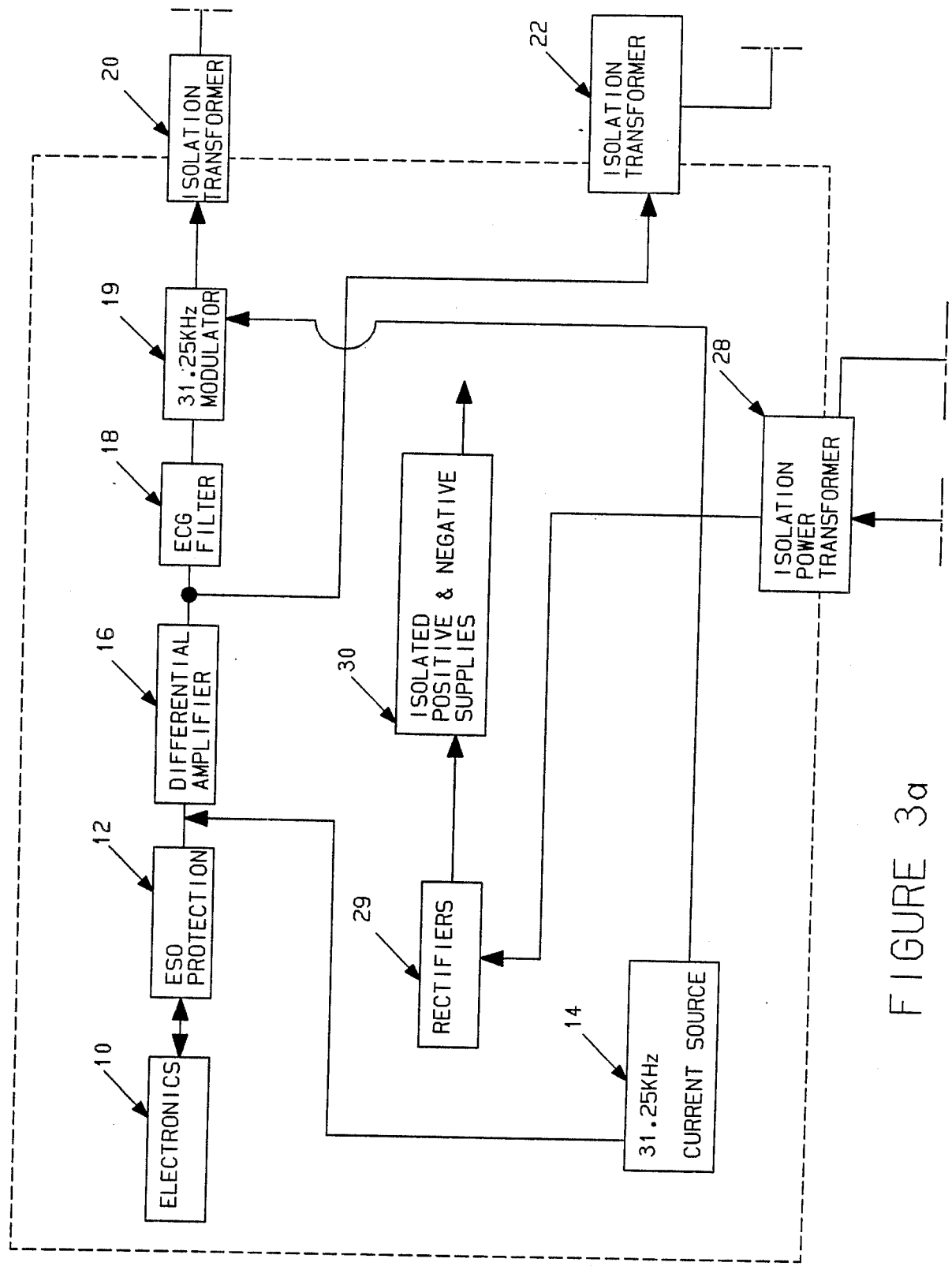
FIGS. 3a–d are a block diagram of the analog circuit board of a medical monitor constructed according to the present invention.
Figure 3B:
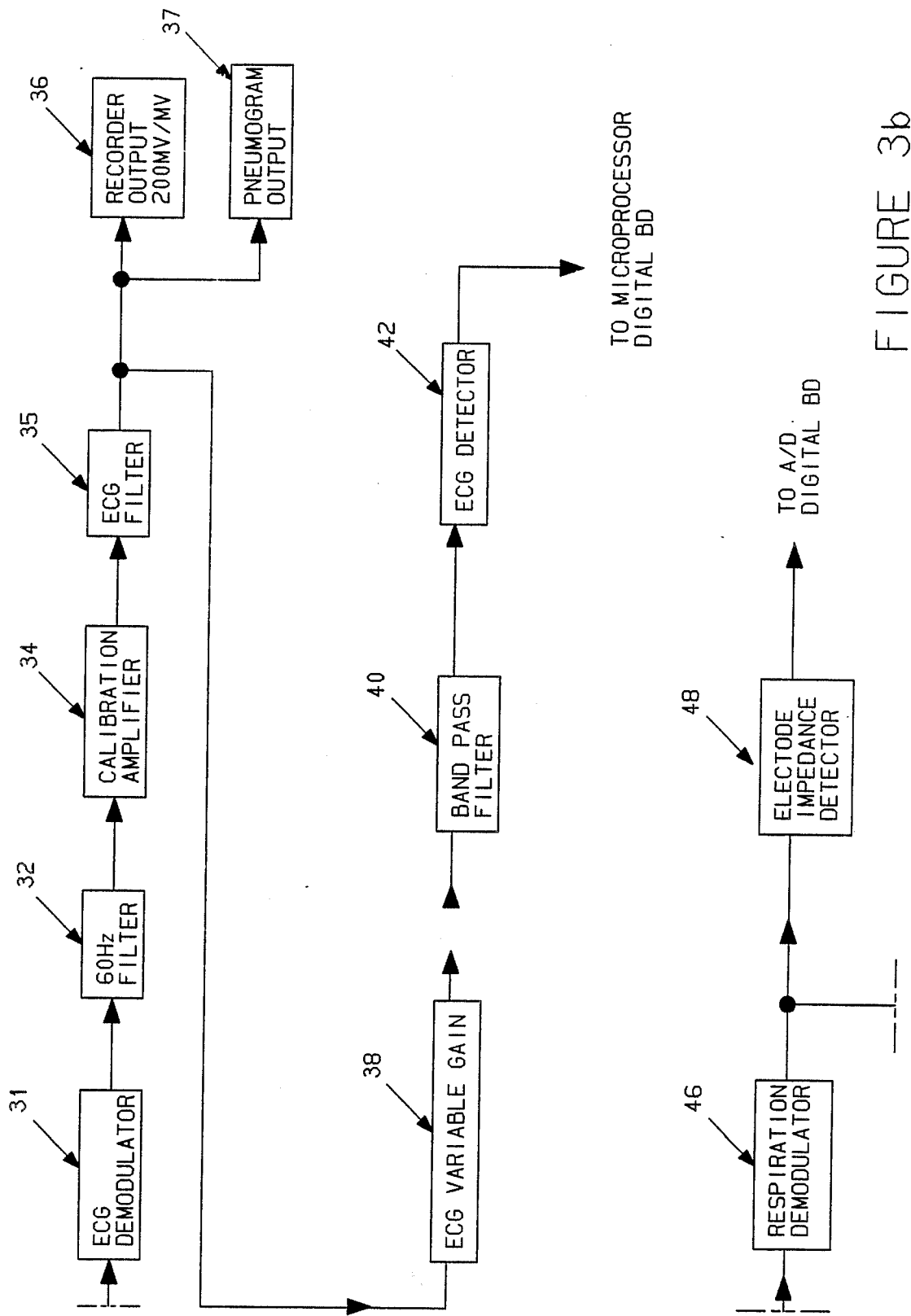
Figure 3C:
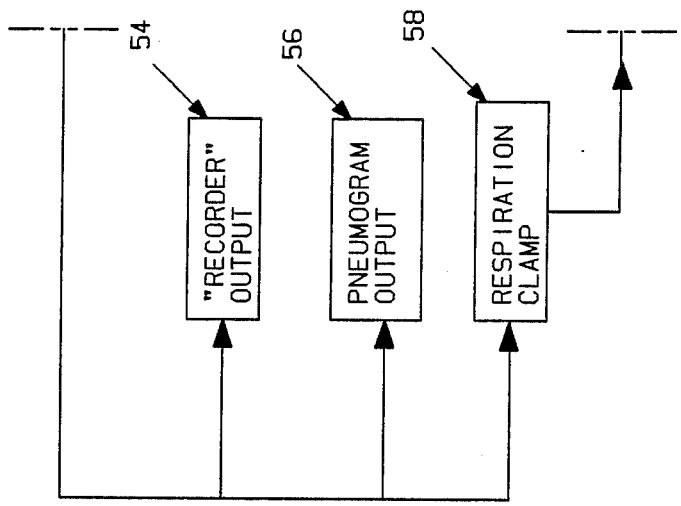
Figure 3C:
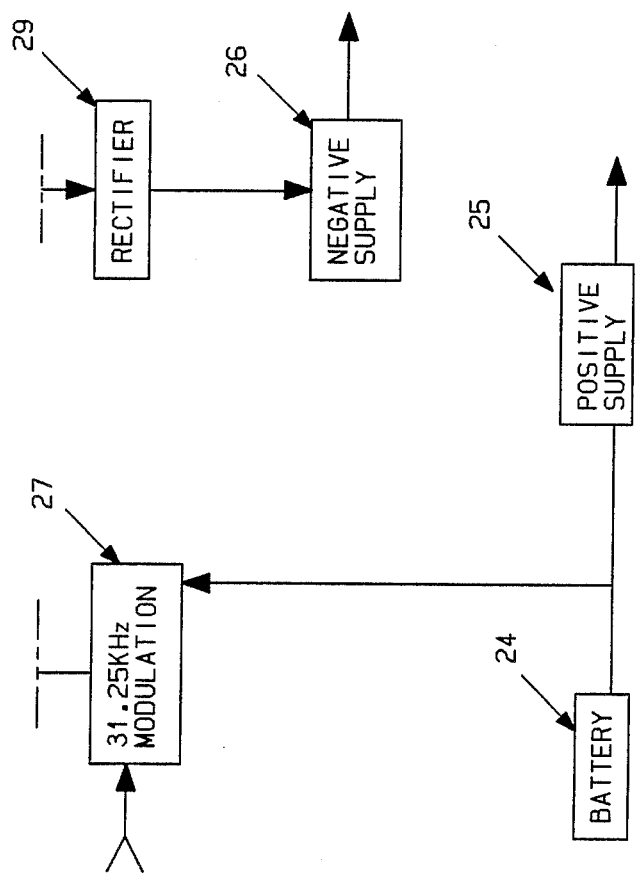
Figure 3D:
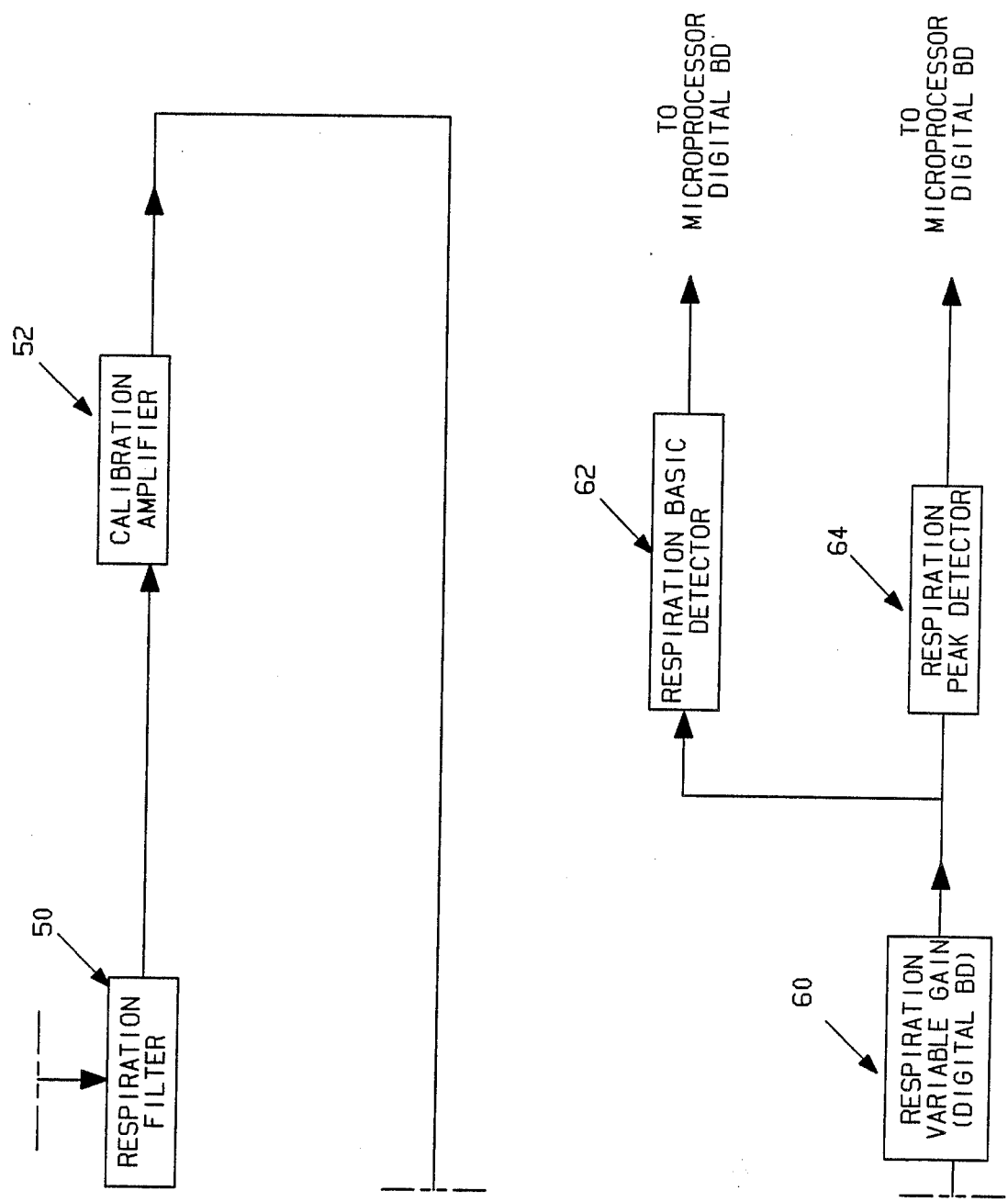

The result of this analysis is illustrated in FIG. 2. The present invention results in discarding artifacts during the apnea. Unlike prior art monitors A, B, and C, the present invention ignores the artifacts and issues an alarm at the end of the set apnea interval. By employing the dual detector apparatus, artifacts are more accurately identified. In this embodiment, the second detector specifically examines the amplitude range of the artifacts and correctly detects them. The input from the two detectors provides the data for the decision-making logic to discard artifacts properly and to sense breaths correctly.

What is claimed is:

1. A medical monitor comprising:
   means for receiving a respiration signal indicative of breathing activity;
   a first detector means, logically connected to the means for receiving, for sensing, at a first sensitivity, a characteristic of the respiration signal and for producing a first event signal indicative of possible breath;
   a second detector means, logically connected to the means for receiving, for sensing, at a second sensitivity, the characteristic of the respiration signal and for producing a second event signal indicative of possible breath;
   means for determining, based upon the first and second event signals, whether a breath occurred.

2. The monitor of claim 1 wherein:
   the characteristic is impedance.

3. The monitor of claim 1 further comprising:
   means for receiving an electical signal indicative of artifact-producing body events; and
   wherein the means for determining further bases its determination on the electrical signal.

4. The monitor of claim 3 wherein:
   the electical signal is indicative of heart beats.

5. The monitor of claim 4 wherein:
   the characteristic is impedance.

6. The monitor of claim 1 wherein:
   the second detector means is a peak detector for sensing peaks in the characteristic.

7. A medical monitor comprising:
   first means for receiving an artifact-coincident signal indicative of an artifact-producing body activity;
   second means for receiving a respiration signal indicative of breathing sensed by patient sensors;
   first detector means, logically connected to the second means for receiving, for determining when amplitude of the respiration signal exceeds a first value, and for producing a first event signal for each event where amplitude exceeds the first value;
   second detector means, logically connected to the second means for receiving, for determining when amplitude of the respiration signal exceeds a second value and for producing a second event signal for each event where amplitude exceeds the second value;

storage means for storing time interval values; and logic means, responsive to event signals and logically connected to the storage means, for:
   receiving each first event signal;
   receiving each second event signal;
   determining a second event time interval since the previous second event signal;
   storing the second event time interval;
   receiving each artifact-coincident signal;
   determining an artifact-coincident tie interval since the previous artifact-coincident signal;
   storing the artifact-coincident time interval; p2 for each first event signal received, comparing the stored artifact-coincident time interval and the stored second event time interval; and
   determining no breath occurred if the artifact-coincident time interval and the second event time interval are generally equal.

8. A medical monitor comprising:
   means for receiving electrical signals from patient electrodes;
   first means for separating from the electrical signals an ECG signal indicative of electrical activity of heart beats;
   second means for separating from the electrical signals a respiration signal indicative of changes in impedance across electrodes;
   a first detector means, logically connected to the second means for separating, for determining when amplitude of the respiration signal exceeds a first value, and for producing a first event signal for each event where amplitude exceeds the first value;
   a second detector means, logically connected to the second means for separating, sensitive to a smaller amplitude, for determining when amplitude of the respiration signal exceeds a second value and for producing a second event signal for each event where amplitude exceeds the second value.

storage means for storing time interval values; and logic means, responsive to event signals and logically connected to the storage means, for:
   receiving each first event signal;
   receiving each second event signal;
   determining a second event time interval since the previous second event signal;
   storing the second event time interval;
   receiving each ECG signal indicative of a heart beat;
   determining an ECG time interval since the previous ECG signal;
   storing the ECG time interval;
   for each first event signal received, comparing the stored ECG interval and the stored second event time interval; and
   determining no breath occurred if the ECG time interval and the second event time interval are generally equal.

9. The monitor of claim 8 wherein:
   the first detector means further comprises a threshold detector which sense amplitude of the respiration signal; and
   the second detector means further comprises a peak detector which senses peaks in amplitude of the respiration signal.

10. A medical monitor comprising:

first means for receiving a patient ECG signal indicative of electrical activity of heart beats;

second means for receiving a patient respiration signal indicative of changes in impedance;

a first detector means, logically connected to the second means for receiving, for determining when amplitude of the respiration signal exceeds a first value, and for producing a first event signal for each event where amplitude exceeds the first value;

a second detector means, logically connected to the second means for receiving, sensitive to a smaller amplitude, for determining when amplitude of the respiration signal exceeds a second value and for producing a second event signal for each event where amplitude exceeds the second value;

storage means for storing breath values associated with second event signals and ECG values associated with ECG signals; and logic means, responsive to event signals and logically connected to the storage means, for:
receiving each first event signal;
receiving each second event signal;
storing a breath value corresponding to each second event signal;
receiving each ECG signal indicative of a heart beat;
storing an ECG value corresponding to each ECG signal;
for each first event signal received, inspecting the stored ECG value and the stored breath value; and
determining, based upon the ECG value and the breath value, whether a breath occurred.

11. The monitor of claim 10 wherein:

the ECG value is indicative of an ECG time interval since the previous ECG signal;

the breath value is indicative of a second event time interval since the previous second event signal; and the means for determining, in the logic means, includes means for deciding that no breath occurred if the ECG time interval and the second event time interval are generally equal.

12. A method for discarding artifacts in a signals used for determining cessations of breathing by a patient, comprising:

sensing a patient ECG signal from patient-mounted electrodes;

determining an ECG time interval since the previous ECG signal;

sensing an impedance change across the electrode above a first amplitude and generating a first event signal;

sensing an impedance change across the electrodes above a second amplitude and generating a second event signal;

determining a second event time interval since the previous second event signal;

for each first event signal, determining that no breath occurred if the ECG time interval is generally equal to the second event time interval.

13. A method for discarding artifacts in signals used for determining cessations of breathing by a patient, comprising:

sensing a patient ECG signal from patient-mounted electrodes;

determining an ECG time interval since the previous ECG signal;

sensing a trait of impedance change across the electrodes at a first sensitivity and generating a first event signal;

sensing the trait of impedance change across the electrode at a second sensitivity and generating a second event signal;

determining a second event time interval since the previous second event signal; and for each first event signal, determining that no breath occurred if the ECG time interval is generally equal to the second event time interval.

14. A medical monitor comprising:

first means for receiving a patient ECG signal indicative of electrical activity of heart beats;

second means for receiving a patient respiration signal indicative of changes ion impedance;

a first detector means, logically connected to the second means for receiving, for determining when a trait of the respiration signal exceeds a first value, and for producing a first event signal for each event where the trait exceeds the first value;

a second detector means, logically connected to the second means for receiving, at a different second sensitivity, for determining when the trait of the respiration signals exceeds a second value and for producing a second event signal for each event where the trait exceeds the second value;

storage means for storing breath value associated with second event signals and ECG values associated with ECG signals; and logic means responsive to event signals and logically connected to the storage means, for:
receiving each first event signal;
receiving each second event signal;
storing a breath value corresponding to each second event signal;
receiving each ECG signal indicative of a heart beat;
storing an ECG value corresponding to each ECG signal;
for each first event signal received, inspecting the stored ECG value and the stored breath value; and
determining, based upon the ECG value and the breath value, whether a breath occurred.

* * * * *